(12) United States Patent
Ryan T. et al.

(10) Patent No.: US 8,467,975 B2
(45) Date of Patent: *Jun. 18, 2013

(54) MIXED LIBRARY PARALLEL GENE MAPPING QUANTITATIVE MICRO-ARRAY TECHNIQUE FOR GENOME-WIDE IDENTIFICATION OF TRAIT CONFERRING GENES

(75) Inventors: Gill Ryan T., Denver, CO (US); Michael D. Lynch, Boulder, CO (US); Tanya E. W. Lipscomb, Boulder, CO (US)

(73) Assignee: The Regents of the University of Colorado, a Body Corporate, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 13/175,929

(22) Filed: Jul. 4, 2011

(65) Prior Publication Data

US 2012/0077681 A1   Mar. 29, 2012

Related U.S. Application Data

(63) Continuation of application No. 11/231,018, filed on Sep. 20, 2005, now Pat. No. 7,987,056.

(60) Provisional application No. 60/611,377, filed on Sep. 20, 2004.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .......... 702/19; 702/22; 703/11; 703/12

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,683,202 A | 7/1987 | Mullis | |
| 5,256,648 A | 10/1993 | Gasparro et al. | |
| 5,484,908 A | 1/1996 | Froehler et al. | |
| 5,543,507 A | 8/1996 | Cook et al. | |
| 5,672,593 A | 9/1997 | Michejda et al. | |
| 5,681,941 A | 10/1997 | Cook et al. | |
| 6,068,977 A | 5/2000 | Perlin | |
| 6,709,861 B2 | 3/2004 | Mead et al. | |
| 7,987,056 B2 | 7/2011 | Gill et al. | |

OTHER PUBLICATIONS

Liu et al. (Gene, 2002, 282, 247-255).*
Gill et al. (PNAS, 2002, 99(10), 7033-7038).*

(Continued)

*Primary Examiner* — Larry D Riggs, II
(74) *Attorney, Agent, or Firm* — Wilson Sonsini Goodrich & Rosati

(57) ABSTRACT

The present disclosure concerns methods and compositions relating to mixed-library parallel gene trait mapping. In particular embodiments, the methods concern quantitative microarray hybridization techniques for genome-wide identification of trait conferring genes. In other embodiments, the compositions concern genetic elements that confer or are associated with a trait. In an exemplary embodiment, the trait is enhanced growth rate. In another exemplary embodiment, genetic elements that confer enhanced bacterial growth rate comprise part or all of the sequences of SEQ ID NO:1, SEQ ID NO:2, SEQ ID NO:3, SEQ ID NO:4 or SEQ ID NO:5. In other embodiments, the genetic elements that confer enhanced bacterial growth rate correspond to the YliF, adrA, yeaP, yddV or ydeH genes of *E. coli*.

14 Claims, 10 Drawing Sheets

OTHER PUBLICATIONS

Antoine, et al. Isolation and molecular characterization of a novel broad-host-range plasmid from *Bordetella bronchiseptica* with sequence similarities to plasmids from gram-positive organisms. Mol Microbiol. 1992; 6(13):1785-1799.

Argaman, et al. Novel small RNA-encoding genes in the intergenic regions of *Escherichia coli*. Curr Biol. 2001; 11(12):941-950.

Badarinarayana, et al. Selection analyses of insertional mutants using subgenic resolution arrays. Nat. Biotechnol. 2001; 19:1060-1064.

Bangham, et al. Multiscale nonlinear decomposition: the sieve decomposition theorem. IEEE Trans. Pattern Anal. Mach. Intell. 1996; 18:529-539.

Bangham, et al. Scale-space from nonlinear filters. IEEE Trans. Pattern Anal. Mach. Intell. 1996; 18:520-529.

Ben-Samoun, et al. Positively regulated expression of the *Escherichia coli* araBAD promoter in *Corynebacterium glutamicum*. FEMS Microbiol Lett. 1999; 174(1):125-130.

Briat, et al. Tau factor from *Escherichia coli* mediates accurate and efficient termination of transcription at the bacteriophage T3 early termination site in vitro. J Mol Biol. 1987; 198(1):43-49.

Brombacher, et al. The curli biosynthesis regulator CsgD co-ordinates the expression of both positive and negative determinants for biofilm formation in *Escherichia coli*. Microbiology. 2003; 149:2847-2857.

Brown, et al. MlrA, a novel regulator of curli (AgF) and extracellular matrix synthesis by *Escherichia coli* and *Salmonella enterica* serovar Typhimurium. Mol. Microbiol. 2001; 41:349-363.

Chawla, et al. Transposition-induced structural instability of *Escherichia coli*- mycobacteria shuttle vectors. Plasmid. 1999; 41(2):135-140.

Cho, et al. Parallel analysis of genetic selections using whole genome oligonucleotide arrays. Proc. Natl. Acad. Sci. USA. 1998; 95:3752-3757.

Covert, et al. Integrating high-throughput and computational data elucidates bacterial networks. Nature. 2004; 429:92-96.

Cronin, et al. pUCP-Nco and pUCP-Nde: *Escherichia—Pseudomonas* shuttle vectors for recombinant protein expression in *Pseudomonas*. Anal Biochem. 1999; 272(1):112-115.

De Lorenzo, et al. Analysis of *Pseudomonas* gene products using lacIq/Ptrp-lac plasmids and transposons that confer conditional phenotypes. Gene. 1993; 123(1):17-24.

Derisi, et al. Exploring the metabolic and genetic control of gene expression on a genomic scale. Science. 1998 278:680-686.

Deshazer, et al. Broad-host-range cloning and cassette vectors based on the R388 trimethoprim resistance gene. Biotechniques. 1996; 20(5):762-764.

Edwards, et al. The *Escherichia coli* MG1655 in silico metabolic genotype: its definition, characteristics, and capabilities. Proc. Natl. Acad. Sci. USA. 2000; 97:5528-5533.

Elena, et al. Evolution experiments with microorganisms: the dynamics and genetic bases of adaptation. Nat. Rev. Genet. 2003; 4:457-469.

Fodor, et al. Light-directed, spatially addressable parallel chemical synthesis. Science. 1991; 251:767-773.

Garcia, et al. Role of the GGDEF protein family in *Salmonella* cellulose biosynthesis and biofilm formation. Mol. Microbiol. 2004; 54:264-277.

Giaever, et al. Functional profiling of the *Saccharomyces cerevisiae* genome. Nature. 2002; 418:387-391.

Godiska et al. Beyond pUC: Vectors for cloning unstable DNA. In: Kieleczawa J, editor. DNA sequencing: Optimizing the process and analysis. Boston, MA: Jones and Bartlett. 2004; p. 55-75.

Godiska et al. Construction of genomic libraries from unclonable DNA. (cited 2005 Jul. 27, 2005; presentation). Available from: http://www.lucigen.com/techinfo/sci_; presentations.html.

Guzman, et al. Tight regu-lation, modulation, and high-level expression by vectors con-taining the arabinose PBAD promoter. J Bacteriol. 1995; 177(14): 4121-4130.

Hickman, et al. A chemosensory system the regulates biofilm formation through modulatiaon of cyclic diguanylate levels. Proc. Natl. Acad. Sci. USA. 2005; 102:14422-14427.

Ibarra, et al. *Escherichia coli* K-12 undergoes adaptive evolution to achieve in silico predicted optimal growth. Nature. 2002; 420:186-189.

Ippen, et al. New controlling element in the Lac operon of *E. coli*. Nature. 1968; 217(131):825-827.

Jenal. Cyclic di-guanosine-monophosphate comes of age: a novel secondary messenger involved in modulating cell surface structures in bacteria? Curr. Opin. Microbiol. 2004; 7:185-191.

Karlyshev, et al. Application of high-density array-based signature-tagged mutagenesis to discover novel *Yersinia* virulence-associated genes. Infect. Immun 2001; 69:7810-7819.

Kirillina, et al. HmsP, a putative phosphodiesterase, and HmsT, a putative diguanylate cyclase, control Hms-dependent biofilm formation in *Yersinia pestis*. Mol. Microbiol. 2004; 54:75-88.

Kovach, et al. Four new derivatives of the broad-host-range cloning vector pBBR1MCS, carrying different antibiotic-resistance cassettes. Gene. 1995; 166(1):175-176.

Labes, et al. A new family of RSF1010-derived expression and lac-fusion broad-host-range vectors for gram-negative bacteria. Gene. 1990; 89(1):37-46.

Li, et al. Characterization of quantitative trait loci (QTLs) in cultivated rice contibuting to field reistance to sheath blight (*Rhizoctonia solani*). Theor Appl Genet. 1995; 91:382-388.

Lio, et al. Wavelets in bioinformatics and computational biology: state of art and perspectives. Bioinformatics Review. 2003; 19(1):2-9.

Lynch, et al. Broad host range vectors for stable genomic library construction. Biotechnology and Bioengineering. May 5, 2006; 94(1):151-158.

Lynch, et al. SCALEs: multiscale analysis of library enrichment. Nat Methods. Jan. 2007;4(1):87-93.

Markie, et al. New vector for transfer of yeast artificial chromosomes to mammalian cells. Somatic Cell and Molecular Genetics. 1993; 19(2):161-169.

Matthysse, et al. Construction of GFP vectors for use in gram-negative bacteria other than *Escherichia coli*. FEMS Microbiol Lett. 1996; 145(1): 87-94.

McKinney, et al. Tightly regulated gene expression system in *Salmonella enterica*serovar Typhimurium. J Bacteriol. 2002; 184(21):6056-6059.

Mobitec. Broad host range vectors pBBR122 and pBHR1. [web page] 2005 (cited 2005 Jul. 25, 2005; Vector Product Page). Available from: http://www.mobitec.de/download/dsheets/pBBR122pBHR1.pdf.

Naef, et al. Solving the riddle of the bright mismatches: labeling and effective binding in oligonucleotide arrays. Phys. Rev. E. 2003; 68:011906.

Newman, et al. Broad-host-range expression vectors that carry the L-arabinose-inducible *Escherichia coli* araBAD promoter and the araC regulator. Gene. 1999; 227(2):197-203.

Ochsner, et al. GeneChip expression analysis of the iron starvation response in *Pseudomonas aeruginosa*: Identification of novel pyoverdine biosynthesis genes. Mol Microbiol. 2002; 45(5):1277-1287.

Office action dated Feb. 24, 2010 for U.S. Appl. No. 11/231,018.
Office action dated Mar. 12, 2009 for U.S. Appl. No. 11/231,018.
Office action dated Aug. 6, 2008 for U.S. Appl. No. 11/231,018.
Office action dated Sep. 3, 2009 for U.S. Appl. No. 11/231,018.
Office action dated Oct. 29, 2010 for U.S. Appl. No. 11/231,018.

Postle, et al. 1985. A bidirectional rho-independent transcription terminator between the *E. coli* tonB gene and an opposing gene. Cell. 1983; 41(2):577-585.

Postle, et al. DNA sequence of the *Escherichia coli* tonB gene. Proc Natl Acad Sci USA. 1983; 80(17):5235-5239.

Quakenbush. Computational Analysis of Microarray Data. Nature Reviews Genetics. 2001; 2:418-427.

Rondon, et al. Toward functional genomics in bacteria: analysis of gene expression in *Escherichia coli* from a bacterila artificial chromosome library of *Bacillus cereus*. Proc. Natl. Acad. Sci. USA. 1999; 96:6451-6455.

Sambrook, et al. Molecular cloning: A laboratory manual, 2nd edition. Cold Spring Harbor: Cold Spring Harbor Laboratory Press. 1989.

Sanchez-Romero, et al. Resistance to tellurite as a selection marker for genetic manipulations of *Pseudomonas* strains. Appl Environ Microbiol. 1998; 64(10):4040-4046.

Santamaria, et al. Premature termination of DNA replication in plasmids carrying two inversely oriented ColE1 origins. J Mol Biol. 2000; 300(1): 75-82.

Schena, et al. Quantitative monitoring of gene expression patterns with a complementary DNA microarray. Science. 1995; 270:467-470.

Sengupta, et al. Relative efficiency of utilization of promoter and termination sites by bacteriophage T3 RNA poly-merase. J Biol Chem. 1989; 264(24):14246-14255.

Shoemaker, et al. Quantitative phenotypic analysis of yeast deletion mutants using a highly parallel molecular bar-coding strategy. Nat. Genet. 1996; 14:450-456.

Simm, et al. GGDEF and EAL domains inversely regulate cyclic di-GMP levels and transition from sessility to motility. Mol. Microbiol. 2004; 53:1123-1134.

Simm, et al. Phenotypic convergence mediated by GGDEF-domain-containing proteins. J. Bacteriol. 2005; 187:6816-6823.

Stueber, et al. Transcription from efficient promoters can interfere with plasmid replication and diminish expression of plasmid specified genes. EMBO J. 1982; 1(11):1399-1404.

Sukchawalit, et al. Construction and characterization of regulated L-arabinose-inducible broad host range expression vectors in Xanthomonas. FEMS Microbiol Lett. 1999; 181(2):217-223.

Szpirer, et al. Interaction between the RP4 coupling protein TraG and the pBHR1 mobilization protein Mob. Mol Microbiol. 2000; 37(6):1283-1292.

Szpirer, et al. Mobilization function of the pBHR1 plasmid, a derivative of the broad-host-range plasmid pBBR1. J Bacteriol. 2001 183(6):2101-2110.

Vieira, et al. New pUC-derived cloning vectors with different selectable markers and DNA replication origins. Gene. 1991; 100:189-194.

Vilette, et al. DNA transcription and repressor binding affect deletion formation in *Escherichia coli* plasmids. EMBO J.1992; 11(10):3629-3634.

Vilette, et al. Transcription-induced deletions in *Escherichia coli* plasmids. Mol Microbiol. 1995; 17(3):493-504.

Vilette, et al. Transcription-induced deletions in plasmid vectors: M13 DNA replication as a source of instability. Mol Gen Genet. 1996; 252(4):398-403.

Winzeler, et al. Functional characterization of the *S. cerevisiae* genome by gene deletion and parallel analysis. Science. 1999; 285:901-906.

Wu, et al. Two divergently transcribed genes, soxR and soxS, control a superoxide response regulon of *Escherichia coli*. J Bacteriol. 1991 173(9):2864-2871.

Zhang, et al. Construction and characterization of two rice bacterial artifical chromosomelibraries from the parents of a permanent recombinant inbred mapping population. Molecular Breeding. 1996; 2:11-24.

Zolg, et al. Characterization of a R plasmid-associated, trimethoprim-resistant dihydrofolate reductase and determination of the nucleotide sequence of the reductase gene. Nucleic Acids Res. 1981; 9(3):697-710.

\* cited by examiner

Fig. 8

TABLE 1.

| Plasmid | Genome Segment Represented | Scale Represented | Average Maximal Growth Rate hr-1 | Relative Growth Rate to vector |
|---|---|---|---|---|
| None (Mach1 T1 no vector) | NA | NA | 0.398 | 1.932 |
| pSmart-LCKan | NA | NA | 0.206 | 1.000 |
| pSLCK-yli-op-1 | moeA-yliG | 12000 | 0.281 | 1.366 |
| pSLCK-yli-op-2 | moeA-yliG | 12000 | 0.247 | 1.200 |
| pSLCK-yli-op-3 | ? | 8000 | 0.297 | 1.444 |
| pSLCK-yli-op-4 | ? | 8000 | 0.323 | 1.571 |

US 8,467,975 B2

MIXED LIBRARY PARALLEL GENE MAPPING QUANTITATIVE MICRO-ARRAY TECHNIQUE FOR GENOME-WIDE IDENTIFICATION OF TRAIT CONFERRING GENES

RELATED APPLICATIONS

The present application is a continuation patent application of U.S. patent application Ser. No. 11/231,018, filed Sep. 20, 2005, now U.S. Pat. No. 7,987,056 which claims the benefit under 35 U.S.C. §119(e) of provisional U.S. patent application Ser. No. 60/611,377, filed on Sep. 20, 2004. These applications are incorporated by reference herein in their entireties.

FEDERALLY FUNDED RESEARCH

The studies disclosed herein were supported in part by grants BES0228584 from the National Science Foundation. The U.S. government may have certain rights to practice the subject invention.

FIELD

The present invention relates to methods and compositions for identification of genetic elements that confer phenotypic traits. In certain embodiments, the methods may involve screening multiple genomic libraries of varying insert size. In particular embodiments, microarray analysis may be used to screen genomic libraries. In more particular embodiments, wavelet based multiresolution data analysis may be used to identify trait-associated or trait-conferring genetic elements.

BACKGROUND

A central goal of functional genomics is to identify genes or other genetic elements (e.g., operons) that are associated with or result in particular phenotypic traits. With the completion of the Human Genome Project and related efforts in other species, a great deal of raw genomic sequence information has become available. However, in many cases the location of expression units (genes) within this vast amount of sequence information remains to be determined. Even where genes or other genetic elements have been identified, their function is frequently unknown.

Both positive and negative phenotypic traits may be conferred by the interplay between genetic elements and environmental conditions. Positive traits may include such characteristics as growth rate, yield, disease resistance, resistance to environmental stresses such as temperature or drought, ability to grow on minimal media, etc. Examples of negative traits might include a predisposition or susceptibility to develop genetically based diseases, such as cancer, heart disease, diabetes and other conditions. In either case, it would be advantageous for the scientist, clinician or other researcher to be able to identify those genetic elements that influence or result in particular traits. Although identification of trait associated genetic elements is of significance in eukaryotes, it is also important in prokaryotes for applications such as biopharmaceutical production, bioremediation, development of chemical tolerance, identification and/or neutralization of antibiotic resistance genes, etc.

A variety of approaches have been attempted to identify trait conferring genetic elements. One approach has been to examine gene expression profiles in different tissues (e.g., diseased vs. normal), at different developmental stages, in response to various environmental factors, or across different physiological classes (e.g., DeRisi et al., 1997 Science 278, 680-685; Roberts et al., 2000, Science 287, 873-880; Schena et al., 1995, Science 270, 467-470). Other approaches have included transformation, gene deletion and complementation studies (see, e.g., Sambrook et al., 1989, Molecular Cloning: A Laboratory Manual, Cold Spring Harbor Laboratory Press, Plainview, N.Y.). Various techniques have utilized deletion libraries marked with identifiable sequences to replace individual genes, analyzed on oligonucleotides or PCR-based spotted microarrays (Winzeler et al., 1999, Science 285, 901-906; Shoemaker et al., 1996, Nat. Genet. 14, 450-456; Badarinarayana et al., 2001, Nat. Biotechnol. 19, 1060-1064). Other alternatives have included overexpression libraries studied by standard plating methodologies (Cho et al., 1998, Proc. Natl. Acad. Sci. USA 95, 3752-3757). More recently, a genome-wide screening technique using hybridization to DNA microarrays has been attempted (Gill et al., 2002, Proc. Natl. Acad. Sci. USA 99:7033-38). Even though DNA microarrays have been used to probe extra-chromosomally based genomic libraries in E. coli, such approaches have been severely limited by a requirement for substantial subcloning of regions of selected chromosomal DNA and, as a consequence, they do not provide quantitative data concerning the effect of overexpression or increased copy on a relevant phenotype.

Despite these efforts, the identification of genes conferring particular traits of interest has lagged significantly behind genome sequencing efforts. One problem with such approaches has been in the identification of a trait conferring gene within inserts containing multiple genes or genetic elements. Another difficulty has been in the detection of trait causing genetic elements against a considerable background of genetic "noise," such as random or unexplained differences in gene expression levels or allele frequencies that are unrelated to the trait of interest. A lack of reproducibility in trait associated gene mapping studies has generally resulted. An unresolved need exists for reliable and reproducible methods and compositions capable of identifying trait associated and/or trait conferring genetic elements.

SUMMARY

The present invention fulfills an unresolved need by providing methods and compositions for the genome wide identification of trait conferring genes. A preferred embodiment concerns a Multi-Library Parallel Gene Trait Mapping (ML-PGTM) method. In various embodiments, that technique may involve the simultaneous screening of several different plasmid libraries of defined insert sizes, followed by micro-array and/or mathematical analyses. The ML-PGTM method is of use to quantitatively pinpoint one or more genetic elements conferring or associated with a trait of interest. The method may be used to effectively sequence thousands of inserts and identify those clones and/or subclones which contain a genetic element that confers a trait. The analysis may also be used to determine the selective advantage of each subclone or clone in a population, giving valuable information regarding a gene's function. For example if one subclone, identifying a single gene (e.g. an enzyme) is sufficient for a trait, yet a larger clone including a transporter provides further amplification of the same trait, hypotheses may be generated and tested regarding the mechanism(s) by which those gene(s) act to confer a trait.

Various embodiments concern compositions comprising isolated nucleic acids. The nucleic acids may comprise sequences of one or more genetic elements that confer a trait. In exemplary embodiments, the nucleic acids may confer the trait of growth rate enhancement in prokaryotes. In particular embodiments, the isolated nucleic acids may comprise any part or all of the sequences disclosed in SEQ ID NO:1-6. Those sequences correspond to nucleotides 865,108 to 876,944 (YliF, SEQ ID NO:1); 402,893 to 405,965 (adrA, SEQ ID NO:2); 1,874,136 to 1,877,094 (yeaP, SEQ ID NO:3); 1,562,990 to 1,565,632 (yddV, SEQ ID NO:4); 1,620,874 to 1,622,633 (ydeH, SEQ ID NO:5) of the E. coli K12 genomic sequence (GenBank Accession No. NC_000913, ATCC Deposit No. 29425). The isolated nucleic acids may be single stranded, double stranded and/or triple stranded.

Other embodiments concern vectors comprising isolated nucleic acids as discussed above. Any type of vector known in the art may be used. The vectors may be expression vectors, with one or more promoters operably linked to the isolated nucleic acids. Vectors that may be of use in the claimed methods and compositions may include, for example, any of those disclosed in U.S. Provisional Patent Application Ser. No. 60/708,177, entitled "Broad Host Range Vectors for Shotgun and Expression Library Cloning in Gram Negative Bacteria," filed Aug. 15, 2005, the entire text of which is incorporated herein by reference. Other exemplary vectors of use may include plasmid, cosmid, BAC, YAC, bacteriophage, viral, retroviral or any other known vectors. Non-limiting examples of particular vectors of use include the pSMART™ LCKan plasmid (Lucigen, Middleton, Wis.) and the pEZSeq vector (Lucigen Corp., Middleton, Wis.).

Still other embodiments concern transformed bacteria comprising a vector as discussed above. In preferred embodiments, the bacteria is a Gram negative bacteria. In more preferred embodiments, the bacteria is a strain of E. coli, such as E. coli K12. In an exemplary embodiment, the bacteria may be the MACH1™-T1$^R$ (Invitrogen) strain of E. coli. A wide variety of techniques for bacterial transformation are known in the art and any such known technique may be used, including but not limited to protoplast fusion, electroporation, bacteriophage mediated transformation, liposomal uptake, etc. Exemplary methods for protoplast fusion based transformation methods are disclosed in U.S. Provisional Patent Application Ser. No. 60/701,242, entitled, "Method for efficient generation, fusion and recovery of protoplasts of Gram negative bacteria," filed Jul. 21, 2005, the entire text of which is incorporated herein by reference. In various embodiments, the isolated nucleic acid and/or vector may become chromosomally incorporated or may be extrachromosomal (episomal).

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 8. Growth Rates for genomic segments. Maximal growth rates were calculated from growth curves performed in 96 well format.

DESCRIPTION OF ILLUSTRATIVE EMBODIMENTS

Definitions

Terms that are not otherwise defined herein are used in accordance with their plain and ordinary meaning.

As used herein, "a" or "an" may mean one or more than one of an item.

As used herein "operably linked" and "operably coupled" refer to a functional linkage between a promoter and/or other regulatory element and a second nucleic acid sequence, wherein the promoter initiates and mediates transcription of the second sequence.

As used herein, a "genetic element" includes genes, gene products (such as RNA molecules and polypeptides), assemblages of more than one gene (e.g., operons), cis-acting regulatory elements (e.g., promoters, enhancers, transcription factor binding sites) and/or trans-acting regulatory elements. Any sequence or assemblage of nucleic acids that may affect the phenotype of a cell containing the sequence or assemblage may constitute a "genetic element".

A genetic element may be said to "confer" a trait when the genetic element, alone or in combination with other genetic elements, when introduced into a host bacterial cell line is sufficient to either provide that trait to a bacterial cell line that did not exhibit the trait in its native (non-transformed) state, or to increase the expression of the trait over its baseline level in the native state. A genetic element may be said to be "associated" with a trait when the removal or inhibition of the genetic element in a bacterial cell line results in an increased or decreased level of expression of the trait, or when the addition of the genetic element to a bacterial cell line results in an increased or decreased level of expression of the trait. Generally, a genetic element that "confers" a trait would be expected to have a direct effect on the trait, while a genetic element "associated" with a trait might be expected to act indirectly upon other genetic elements that "confer" the trait.

Mixed-Library Parallel Gene Trait Mapping

The Mixed-Library Parallel Gene Trait Mapping (ML-PGTM) method disclosed herein may be used to simultaneously map the effect of thousands of genes on a desired trait or phenotype. In certain embodiments, the method involves selection of a mixture of plasmid based genomic libraries of varying insert sizes. Micro-array analysis of enriched plasmid DNA, along with a wavelet based multiresolution analysis precisely identifies the relevant genetic elements.

This technique allows for the identification of single open reading frames as well as larger fragments, such as operons, that confer or amplify a given phenotype. In one exemplary embodiment of the ML-PGTM method, *E. coli* transformants were selected for increased growth rate in minimal media using genomic libraries with 0.5 kb, 1 kb, 2 kb, 4 kb and 8 kb insert sizes.

Figure 1:
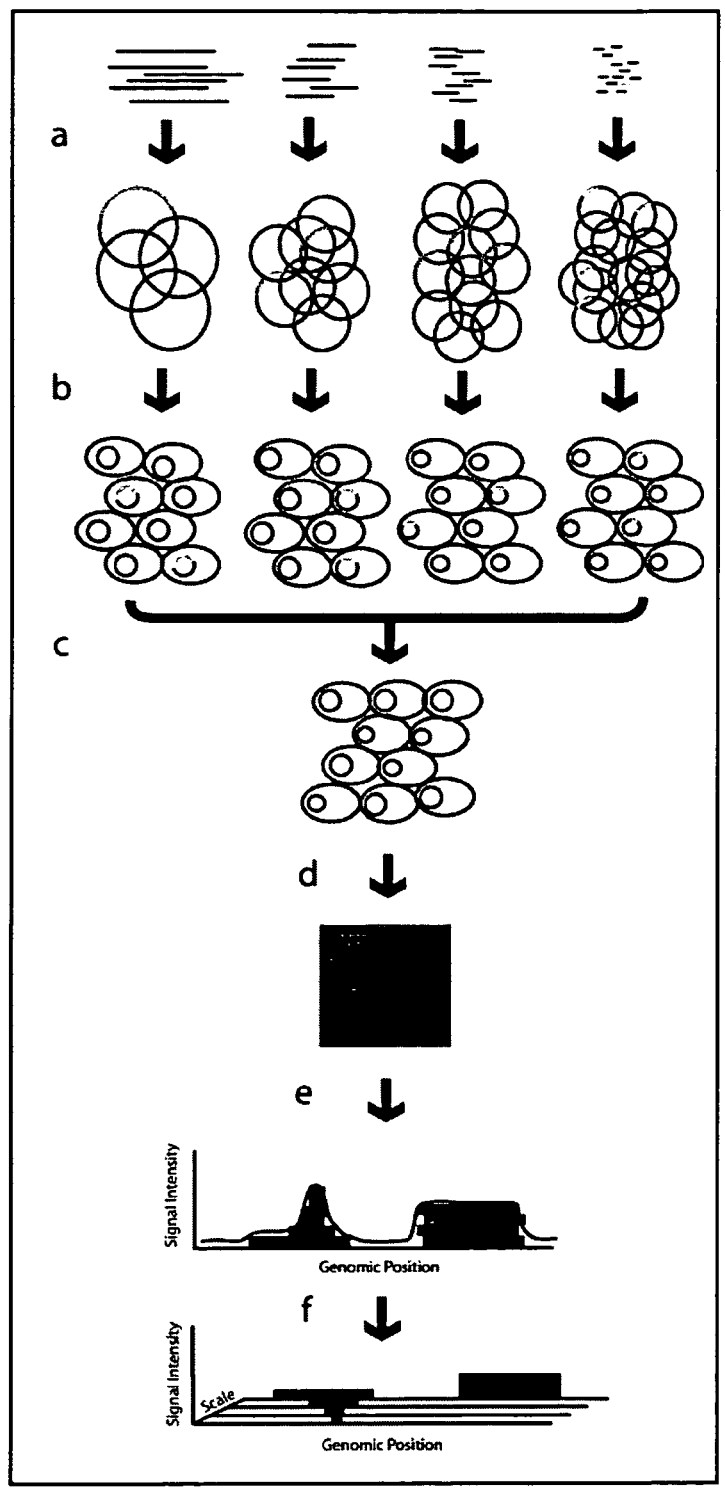
FIG. 1 shows an exemplary overview of Mixed Library Parallel Gene Trait Mapping. a) Genomic DNA fragmented to several specific sizes is ligated into vectors creating several libraries with defined insert sizes. b) These libraries are individually transformed into the cell line used for selections. c) The pools of transformants are mixed and subjected to selection. Only clones bearing plasmids with inserts increasing fitness survive. d) Plasmids are purified from the selected population, prepared for hybridization and applied to a micro-array. e) After analyzing the micro-array signal, the signal is plotted as a function of sequence position. f) A multiresolution analysis utilizing wavelets gives the signal not only as a function of position but also of scale or library size. This data can be used to pinpoint the genetic elements of interest.

An overview of ML-PGTM is depicted in FIG. 1. Briefly, several plasmid libraries are constructed with the DNA to be screened. The libraries are of defined insert sizes. In the non-limiting Example disclosed below, inserts were increased by multiples of two for simplified subsequent mathematical analyses. These libraries are individually transformed into the cell line to be screened. Transformed populations are mixed and subjected to selection for a desired trait, in one exemplary embodiment the trait of enhanced growth rate. Enriched plasmids are purified from the selected population, labeled and hybridized to a DNA micro-array. Micro-array probe level signals are plotted as a function of genome position. This signal is then subjected to a wavelet based multiresolution analysis, which decomposes the signal into scales or the signal contribution from each of the defined sized libraries.

Selections performed on such mixed libraries would produce unique signal intensity patterns along the genome that would indicate specific combinations of genes or regions required for altered growth. That is, for phenotypes resulting from the overexpression of short pieces of genomic DNA (i.e., a single gene, sRNA or perhaps DNA binding motif), enrichment of the insert DNA would occur in each of the libraries constructed and result in a sharp signal intensity peak corresponding to the gene of interest. In contrast, for those phenotypes dependent upon the overexpression of a larger region of genomic DNA (i.e. an operon), enrichment would occur only in those libraries containing the largest insert DNA leading to a broad signal intensity peak corresponding to the relevant genes.

As disclosed in the Examples below, using this approach, we have measured genome-wide, quantitative growth data for *E. coli* and have identified several genomic regions for which increased copy improves growth rate in minimal media by 50% when compared to an empty plasmid control. Microarrays and their subsequent analysis identified several smaller genetic elements as well as larger ones to be responsible for the increased growth rate. These results were subsequently confirmed by individual growth experiments. In addition to identifying genes resulting in large increases in growth rate, a detailed analysis is capable of calculating growth rates associated with each scale and position across the entire genome, providing true genome wide trait mapping. this approach is widely applicable for studying increased copy or mutation affects in other organisms. Furthermore, this approach may be combined with microarray enabled insertional mutagenesis approaches to enable comprehensive and rapid studies of the effect of duplication, mutation and/or disruption on cellular phenotypes.

Data Analysis

In various embodiments, the data analysis used in the ML-PGTM method provides a genome-wide, quantitative identification of genetic elements conferring or associated with a trait. The following discussion provides one non-limiting example of how data analysis may be performed in the ML-PGTM method.

Microarray Signal Extraction

Affymetrix *E. Coli* Antisense Gene Chip arrays (Affymetrix) were hybridized with genomic libraries containing different inserts of defined length and scanned according to the *E. Coli* expression protocol from Affymetrix, producing affymetrix.cel files. Raw chip signals were extracted from the Affymetrix files. Probe signals were extracted and grouped by affinity. These groupings were based on the predicted probe affinities suggested by Magnasco & Naef, (2003, Phys Rev E Stat Nonlin Soft Matter Phys. 68(1 Pt 1)).

The background for each probe was subtracted by a MAS 5.0 type algorithm, where the weighted average of the lowest 2% of signals from 16 chip sections were used as a measure of background.

The perfect match signal was robustly regressed against the PM-MM signals for each group. The intercept of this regression served as a measure of nonspecific signal for the probes in this group. This signal was subtracted from each probe.

Chips were normalized using a set of 5 positive control probe plasmids. These control concentrations were applied equally to each array in a range from 0 pM to 0.5 pM. Normalization was done by fitting signal intensity to a logarithmic function of the positive control probe concentration. These fit curves were used to estimate concentrations from each array for all probe signals.

Multiresolution Analysis

A Wavelet based multiresolution analysis was applied to the corrected probe signals from each chip. This was done using a modified Haar Scaling function. Rather than a direct averaging, a Tukey biweight was applied to achieve more robust estimates. The signal attributable to a given scale at a given position was calculated as the tukey biweight estimate of all probes within a half a scales distance in either direction from the position in question. This was done for 8000 bp, 4000 bp, 2000 bp, 1000 bp and 500 bp scales, if the density of probes in a given region permitted all scales to be calculated. At any position the scale signals were normalized such that their sum was equal to the original signal at that position. This original signal was estimated by the signal of the smallest scale available.

Growth rates for a given scale centered at a given position were calculated using a standard Monod equation, substituting the scale signals as estimations of concentrations.

Micro-Arrays

In particular embodiments, the methods disclosed herein may utilize one or more microarray devices for analysis of genetic elements. It is contemplated that any type of microarray known in the art may be used. A variety of nucleic acid microarrays are known and/or are commercially available. For example, *E. Coli* Antisense Gene Chip arrays (Affymetrix, Santa Clara, Calif.), may be of use in specific embodiments. Generally, microarrays will comprise ordered arrays of nucleic acids, such as nucleic acid probes, that are covalently or non-covalently attached to a chip surface (e.g., Schena, ed., "DNA Microarrays A Practical Approach," Oxford University Press; Marshall et al. (1998) Nat. Biotechnol. 16:27-31; each incorporated herein by reference).

Nucleic Acids

In various embodiments, isolated nucleic acids may encode proteins that confer or are associated with a trait. In other embodiments, the nucleic acid itself may confer or be associated with a trait. The isolated nucleic acid may be derived from genomic DNA, complementary DNA (cDNA) or synthetic DNA.

A "nucleic acid" includes single-stranded and double-stranded molecules, as well as DNA, RNA, chemically modified nucleic acids and nucleic acid analogs. It is contemplated that a nucleic acid may be of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater nucleotide residues in length, up to a full length protein encoding or regulatory genetic element. In some cases, nucleic acids may comprise one or more genes.

In certain embodiments, proteins and/or peptides of interest may be encoded by any nucleic acid sequence that encodes the appropriate sequence of amino acids. The skilled artisan is aware that alternative nucleic acid sequences may be used to encode the same trait-conferring protein. In various embodiments, native nucleic acid sequences encoding selected proteins or peptides may be used in the claimed methods and compositions. In alternative embodiments, synthetic nucleic acids encoding the same or a similar amino acid sequence may be used. The design and production of nucleic acids encoding a desired amino acid sequence is well known to those of skill in the art, using standardized codon tables well known in the art. The codons selected for encoding each amino acid may be modified to optimize expression of the nucleic acid in the host cell of interest, for example by using codons optimized for expression in Gram negative or other types of bacteria. Codon preferences for various species of host cell are well known in the art.

Construction of Nucleic Acids

Isolated nucleic acids may be made by any method known in the art, for example using standard recombinant methods, synthetic techniques, or combinations thereof. In some embodiments, the nucleic acids may be cloned, amplified, or otherwise constructed.

The nucleic acids may conveniently comprise sequences in addition to a trait conferring or trait associated genetic element. For example, a multi-cloning site comprising one or more endonuclease restriction sites may be added. Regulatory sequences may be added to promote expression of the nucleic acid. A nucleic acid may be attached to a vector, adapter, or linker for cloning and/or expression of a nucleic acid. Additional sequences may be added to such cloning and/or expression sequences to optimize their function in cloning and/or expression, to aid in isolation of the nucleic acid, or to improve the introduction of the nucleic acid into a cell. Use of cloning vectors, expression vectors, adapters, and linkers is well known in the art.

Recombinant Methods for Constructing Nucleic Acids

Isolated nucleic acids may be obtained from bacterial or other sources using any number of cloning methodologies known in the art. In some embodiments, oligonucleotide probes which selectively hybridize, under stringent conditions, to the nucleic acids are used to identify a sequence in a genomic DNA library. Methods for construction of genomic libraries are known and any such known methods may be used. [See, e.g., Current Protocols in Molecular Biology, Ausubel, et al., Eds., Greene Publishing and Wiley-Interscience, New York (1995); Sambrook, et al., Molecular Cloning: A Laboratory Manual, 2nd Ed., Cold Spring Harbor Laboratory Vols. 1-3 (1989); Methods in Enzymology, Vol. 152, Guide to Molecular Cloning Techniques, Berger and Kimmel, Eds., San Diego: Academic Press, Inc. (1987).]

Nucleic Acid Screening and Isolation

Genomic libraries, transgenic or native bacteria may be screened for the presence and/or expression levels of an identified genetic element of interest using a probe based upon one or more sequences, such as those disclosed in SEQ ID NO:1-5. Various degrees of stringency of hybridization may be employed in the assay. As the conditions for hybridization become more stringent, there must be a greater degree of complementarity between the probe and the target for duplex formation to occur. The degree of stringency may be controlled by temperature, ionic strength, pH and/or the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, minor sequence variations in the probes and primers may be compensated for by reducing the stringency of the hybridization and/or wash medium.

High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture. Nucleic acids may be completely complementary to a target sequence or may exhibit one or more mismatches.

Nucleic Acid Amplification

Nucleic acids of interest may also be amplified using a variety of known amplification techniques. For instance, polymerase chain reaction (PCR) technology may be used to amplify target sequences directly from genomic DNA or vector insert sequences. PCR and other in vitro amplification methods may also be useful, for example, to clone nucleic acid sequences that code for proteins to be expressed, to make nucleic acids to use as probes for detecting the presence of a target nucleic acid in samples, for nucleic acid sequencing, or for other purposes. Examples of techniques of use for nucleic acid amplification are found in Berger, Sambrook, and Ausubel, as well as Mullis et al., U.S. Pat. No. 4,683,202 (1987); and, PCR Protocols A Guide to Methods and Applications, Innis et al., Eds., Academic Press Inc., San Diego, Calif. (1990). PCR-based screening methods have been disclosed. [See, e.g., Wilfinger et al. BioTechniques, 22(3): 481-486 (1997).]

Synthetic Methods for Constructing Nucleic Acids

Isolated nucleic acids may be prepared by direct chemical synthesis by methods such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetra. Lett. 22:859-1862 (1981); the solid phase phosphoramidite triester method of Beaucage and Caruthers, Tetra. Letts. 22(20):1859-1862 (1981), using an automated synthesizer as in Needham-VanDevanter et al., Nucleic Acids Res., 12:6159-6168 (1984); or by the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. While chemical synthesis of DNA is best employed for sequences of about 100 bases or less, longer sequences may be obtained by the ligation of shorter sequences.

Covalent Modification of Nucleic Acids

A variety of cross-linking agents, alkylating agents and radical generating species may be used to bind, label, detect, and/or cleave nucleic acids. For example, Vlassov, V. V., et al., Nucleic Acids Res (1986) 14:4065-4076, disclose covalent bonding of a single-stranded DNA fragment with alkylating derivatives of nucleotides complementary to target sequences. A report of similar work by the same group is that by Knorre, D. G., et al., Biochimie (1985) 67:785-789. Iverson and Dervan also showed sequence-specific cleavage of single-stranded DNA mediated by incorporation of a modified nucleotide which was capable of activating cleavage (J Am Chem Soc (1987) 109:1241-1243). Meyer, R. B., et al., J Am Chem Soc (1989) 111:8517-8519 disclose covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197-3203. Use of crosslinking in triple-helix forming probes was also disclosed by Home, et al., J Am Chem Soc (1990) 112:2435-2437. Use of N4,N4-ethanocytosine as an alkylating agent to crosslink to single-stranded oligonucleotides has also been disclosed by Webb and Matteucci, J Am Chem Soc (1986) 108:2764-2765; Nucleic Acids Res (1986) 14:7661-7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Expression Vectors

Various embodiments concern vectors comprising trait conferring nucleic acids, which vectors may be transformed into a target host cell. An expression vector will typically comprise a nucleic acid operably linked to transcriptional regulatory elements which will direct the transcription of the nucleic acid. For example, expression vectors may include a cloned growth enhancing or other trait conferring genetic element under the transcriptional control of 5' and/or 3' regulatory sequences. Expression vectors may contain a promoter sequence (e.g., one conferring inducible or constitutive, environmentally- or developmentally-regulated expression), a ribosome binding site, a start codon, a transcription termination site, and/or an origin of replication.

The vector comprising a nucleic acid will typically comprise a marker gene that confers a selectable phenotype on transformed cells. Usually, the selectable marker gene will encode antibiotic resistance, with suitable genes including genes coding for resistance to antibiotics such as beta-lactamase (penicillin resistance), streptomycin resistance, kanamycin resistance, or other such genes known in the art. Methods for selecting transformed cells using marker genes and selective agents are known in the art. Alternatively, screenable marker genes such as GUS or beta-galactosidase may be used.

EXAMPLES

The following examples are included to illustrate various embodiments of the invention. It should be appreciated by those of skill in the art that the techniques disclosed in the examples which follow represent techniques discovered to function well in the practice of the claimed methods. However, those of skill in the art should, in light of the present disclosure, appreciate that many changes may be made in the specific embodiments which are disclosed and still obtain a like or similar result without departing from the spirit and scope of the invention.

Example 1

Mixed Library Parallel Gene Trait Mapping

Methods and Materials

Bacteria, Plasmids, and Media

Wild-type *Escherichia coli* K12 (ATCC #29425) was used for the preparation of genomic DNA. Genomic libraries were constructed using the pSMART™ LCKan plasmid (Lucigen, Middleton, Wis.). Cultures for library construction were cultivated in Luria-Bertani (LB) media at 37° C. Continuous chemostat cultures were carried out with MOPS Minimal Medium (Neidehardt 1974). Antibiotic concentrations used were 20 µg kanamycin/ml, 100 µg chloramphenicol/ml.

Genomic Library Construction

Overnight cultures of the *E. coli* strain K12 were cultivated in 150 ml of LB at 37° C. to an optical density of 1.0 measured by absorbance at 600 nm. The culture was centrifuged at 5000 rpm, 4° C. for 15 min. The cell pellet was then washed in 50 ml of TES buffer: 10 mM Tris HCl, 1 mM EDTA 1.5% w/v NaCl, pH=8.0 and again centrifuged. The pellet was again resuspended in 50 ml of TES buffer. 300 µl of 20 mg/ml proteinase K (Fisher) and 3 ml of 10% w/v SDS were added to the cell suspension which was then incubated at 55° C. for 16 hours. The genomic DNA was then extracted twice with equal volumes of TE (10 mM Tris HCl, 1 mM EDTA, pH=8.0) saturated phenol followed by two extractions with TE saturated phenol/chloroform/isoamyl alcohol (25:24:1). Genomic DNA was then precipitated with 1/10 volume 3 M NaOAc pH=5.5 and 0.6 volumes of isopropanol. DNA pellets were washed with 70% ethanol and resuspended in TE buffer pH=8.0.

Six samples of 50 ng of purified genomic DNA were digested with two blunt cutters AluI and RsaI (Invitrogen) both having a four base pair long recognition sequence. 50 µl reactions with four units of each enzyme plus 50 mM Tris-HCl (pH 8.0), and 10 mM $MgCl_2$ were carried out for 10, 20 30, 40, 50, and 60 minutes respectively, at 37° C. The reactions were heat inactivated at 70° C. for 15 minutes. Restriction digestions were mixed and the fragmented DNA was separated based on size using agarose gel electrophoresis. DNA fragments of 0.5, 1, 2, 4, and greater than 8 kb were excised from the gel and purified with a Gel Extraction Kit (Qiagen), according to manufacturer's instructions. The purity of the DNA fragments was quantified using UV absorbance each with an $A_{260}/A_{280}$ absorbance ratio of >1.7.

Ligation of the purified, fragmented DNA with the pSMART™ LCKan vector was performed according to manufacturer's instructions (Lucigen, Middleton, Wis.). The ligation product was then electroporated into E. Cloni 10 G Supreme Electrocompetent Cells (Lucigen) and plated on LB+kanamycin. Dilution cultures were inoculated with 1/1000 volume of the original transformations and plated on LB+Kan in order to determine transformation efficiency and transformant numbers Three of these dilutions were plated, in order to get average transformant counts. Plates were incubated overnight at 37° C. for 24 hours.

Colonies were harvested by gently scraping the plates into TB media and incubating at 37° C. for 1 hour. Plasmids were then amplified by adding chloramphenicol to the culture and incubating at 37° C. for 30 minutes before centrifugation at 5000 rpm for 15 minutes. The plasmid DNA was extracted according to manufacturer's instructions using a HiSpeed Plasmid Midi Kit (Qiagen).

In order to confirm insert sizes and transformant numbers, overnight cultures of clones for each library were inoculated with colonies picked from the dilution plates. Plasmids were purified using a Qiaprep Spin MiniPrep Kit from Qiagen. The plasmid DNA was then digested with EcoRl. Inspection by electrophoresis showed that greater than 80% of the colonies contained an insert of the expected size.

Colony PCR using the SL1 (5'-CAG TCC AGT TAC GCT GGA GTC-3') (SEQ ID NO:6) and SR2 (5'-GGT CAG GTA TGA TTT AAA TGG TCA GT-3') (SEQ ID NO:7) primers was performed on ten colonies from the 0.5, 1, and 2 kb libraries. PCR confirmed that the colonies contained an insert of the expected size and that chimeras were not present.

Continuous Chemostat Cultures

A continuous culture system was developed with a working volume of 100 ml. MOPS minimal media plus kanamycin was introduced at a controlled volumetric flow rate by use of a peristaltic pump. Similarly, volume was maintained by an outlet pump set to a maximal flow rate at a given depth in the culture vessel. The chemostat conditions were as follows: Agitation was vigorous using a stir plate on the highest setting. Cultures were incubated at 37° C. Filtered house air was introduced for proper aeration through a sparge port. Clones exhibiting an increase in specific growth rate were selected for by increasing dilution rate gradually along the duration of the continuous culture over 100 generations.

Chemostat cultures were performed in duplicate. For each chemostat culture greater than $10^7$ clones were obtained after the transformation of these libraries into MACH1-T1 cells, once again providing adequate representation of the genome at each scale. All transformants were mixed and inoculated into chemostats containing MOPS minimal media. Cell density was monitored in the culture as the dilution rate was systematically increased.

Transformation of Library DNA

Purified plasmid DNA from each library was introduced into MACH1™-T1$^R$ (Invitrogen) by electroporation. MACH1™-T1$^R$ cultures were made electrocompetent by standard glycerol washes on ice to a final concentration of 10 cells/ml. (Molecular Cloning). Dilution cultures were inoculated with 1/1000 volume of the original transformations and plated on LB+Kan in order to determine transformation efficiency and transformant numbers. The original cultures were combined and diluted to 100 ml with MOPS Minimal Media and incubated at 37 C for 6 hours or until reaching an $OD_{600}$ of 0.50. This mixture was then introduced into a chemostat vessel and the initial dilution rate was set to 0.015 min$^{-1}$. The $OD_{600}$ of the culture was recorded every six hours and the dilution rate was adjusted according to the growth.

Sampling

Every 12 hours 100 ml of LB+kan was inoculated with a 100 µl sample collected from the outlet stream. 10 µl of the culture were plated on LB+Kan to obtain colonies for sequencing and further growth studies. The remainder was incubated at 37° C. for 12 hours, with shaking at 225 rpm. Plasmids from these cultures were amplified with chloramphenicol at 37° C. for 30 minutes before centrifugation at 5000 rpm for 15 minutes. The plasmid DNA was extracted using a HiSpeed Plasmid Midi Kit from (Qiagen) and prepared for micro-array hybridization.

Micro-Arrays

For each array, 7.5 µg of sample plasmid DNA was mixed with the following control plasmid DNA, which was similarly purified: 1000 ng pGIBS-DAP (ATCC#87486), 100 ng pGIBS-THR (ATCC#87484), 10 ng pGIBS-TRP (ATCC#87485) and 1 ng pGIBS-PHE (ATCC#87483). The plasmid mixture was digested at 37° C. overnight with 10 units each of AluI and RsaI (Invitrogen) in a reaction containing 50 mM Tris-HCl (pH 8.0), and 10 mM $MgCl_2$. Reactions were heat inactivated at 70° C. for 15 minutes. 10× One Phor All Buffer (Amersham) was added to the digestions to a final 1× concentration. In addition, 2 units of RQDNAse I (Fisher) and 200 units of Exonuclease III (Fisher) were added. These reactions were carried out at 37° C. for 30 minutes followed by heat inactivation at 98° C. for 20 minutes. The fragmented single stranded DNA was then labeled with biotinylated ddUTP using the Enzo Bioarray Terminal Labeling Kit (ENZO) following the manufacturers' protocol.

Affymetrix E. Coli Antisense Gene Chip arrays (Affymetrix) were handled and scanned according to the E. Coli expression protocol from Affymetrix producing affymetrix-.cel files.

Data Analysis

Probe level signals were extracted from the .cel files using the Expression Exporter software (Affymetrix). For each array, in order to subtract background signal as well as any signal from genomic DNA contamination, the largest signal from any pGIBS-LYS (ATCC#87482) probe was subtracted from all probes. This control DNA was not added to the sample and the LYS gene itself is on the chromosome of MACH1-T1, an E. Coli strain W derivative. Next, outlier probes were identified and removed using the Hampel identifier, with probes signals averaged over a 250 bp range to calculate median values. Average signals of positive control probes were fit to a logarithmic function of moles. This was used to calculate the moles due to each signal in the sample. These signals were then mapped to genomic position giving a signal as a function of position. Data was padded by filling genomic positions between probes with a line connecting closest probe pairs. The resulting signal was subjected to a continuous wavelet transform to perform the multiresolution analysis. Every 10 base pairs was given a signal. This signal was subjected to a discrete wavelet transform using a Debauchies mother wavelet and WaveLab v. 8.02 Software (Rice University). The signal was reconstructed after deletion of scales smaller than 500 bp. The resulting denoised signal was subjected to a multiresolution analysis using the same software.

Growth Curves

Growth curves, were obtained with replicates using a PowerWave XS KC4 v3.1 (Biotek, Winooski, Vt.) using the kinetic mode (37° C., shaking intensity-medium) with readings taken every 30 minutes. A 1% v/v of overnight culture was used to inoculate 200 µl of MOPs minimal media plus 20 µg/ml kanamycin, in a flat bottom 96 well plate (Costar model 3370). Optical density measurements were recorded at 977 nm, 900 nm, and 600 nm, and then adjusted according to the manufacturers instructions (adjusted 600=600/((977−900)/0.18)). The adjusted 600 nm reading was used for construction of growth curves. Maximal growth rates were calculated from these curves. Growth rate was calculated as the maximal slope comprising at least 4 time points (2 hours).

Results

Four E. Coli K12 genomic libraries were created in the pSmart-LCKan vector. These libraries consisted of greater than $10^6$ clones with correct insert size in the case of the 0.5 kb, 1 kb, 2 kb and 4 kb libraries, and greater than $10^5$ clones with the correct insert size for the 8 kb library. In each case there is a greater than 99.9% probability that the entire genome is represented. The number of colonies required for a representational library (>99.9% of genome expressed) is dependant on the size of the insert DNA.

Figure 2:
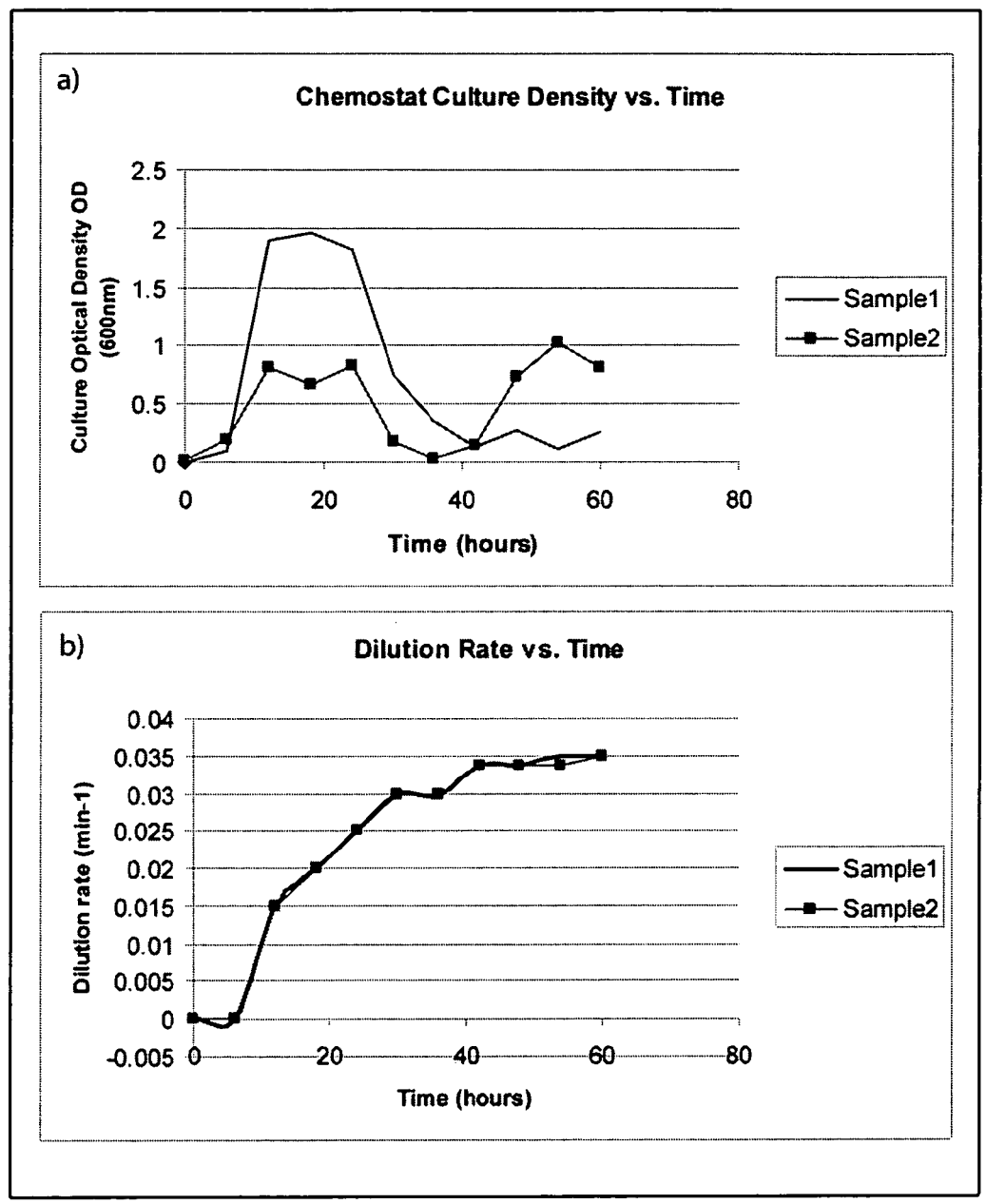
FIG. 2A shows a plot of the culture optical density over time. Culture density was monitored by taking samples from the exit streams of the continuous cultures and taking absorbance readings at 600 nm.
FIG. 2B shows dilution rate for each sample culture plotted vs. time. Increasing the volumetric flow rate of the feed increased the dilution rate over time. The dilution rate per time is calculated by dividing the volumetric flow rate by the culture volume.
Figure 3:
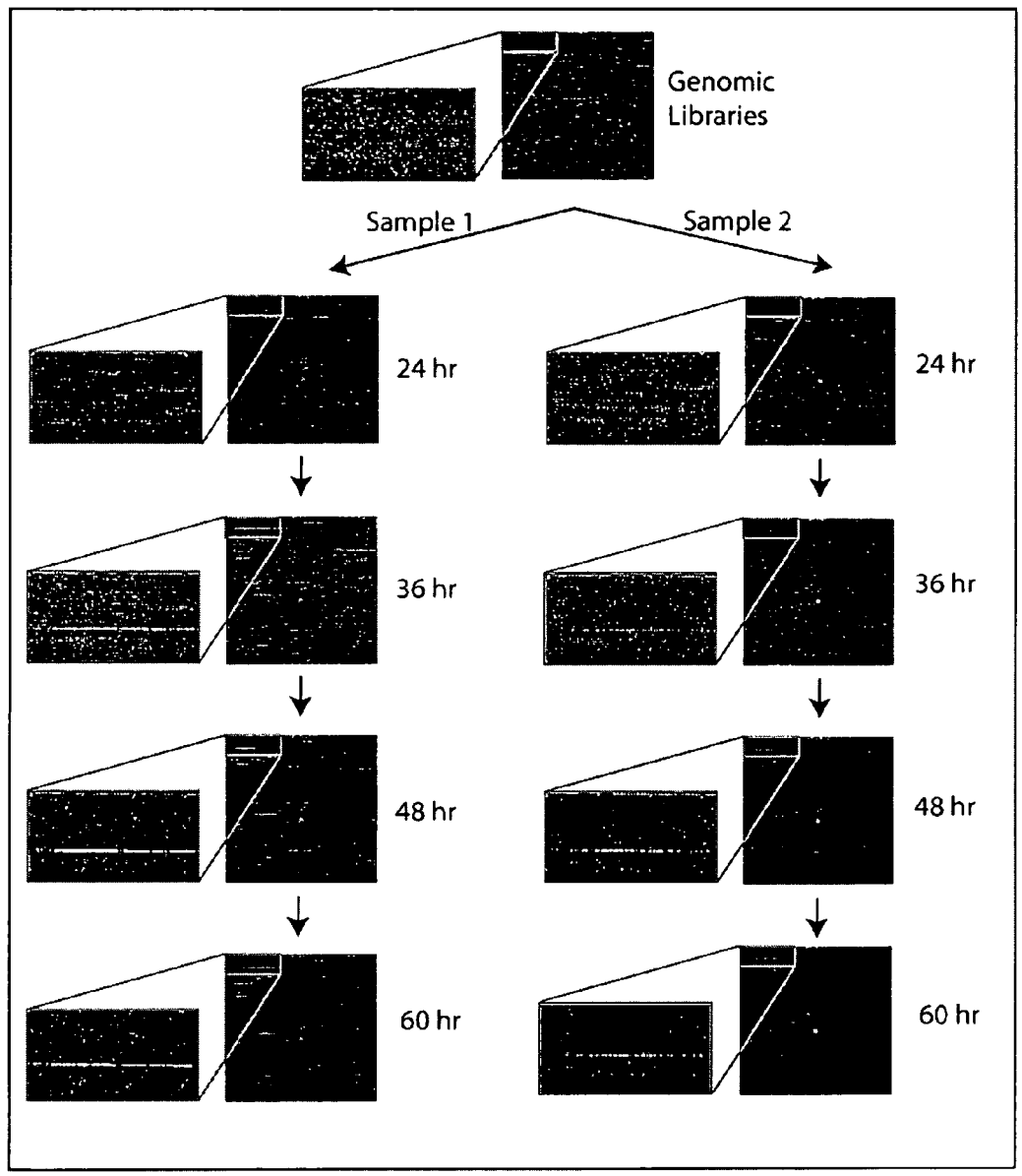
FIG. 3 illustrates micro-array images following the time course of the chemostat selection. Two chemostat cultures were inoculated with a mixture of transformants from each size library. Samples were taken every 12 hours and applied to E. Coli Antisense Affymetix Gene Chips. A magnified panel for each chip shows the signal change for the yli operon in greater detail. Each image was scaled to a similar intensity for clarity.
Figure 4A:
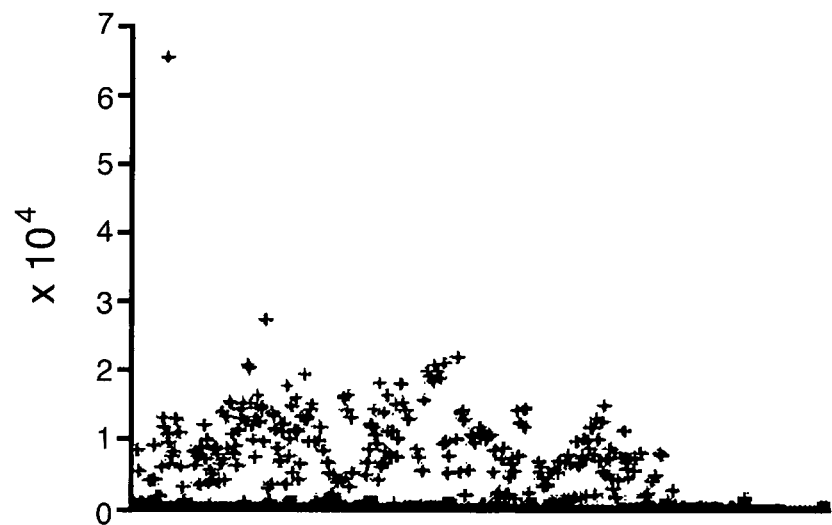
FIG. 4A-4F show an exemplary Wavelet Denoising and Multiresolution Analysis of the yli and yea operons. Raw signals (FIG. 4A for yli, FIG. 4B for yea) are averaged and normalized resulting in a continuous signal (FIG. 4C for yli, FIG. 4D for yea). A continuous wavelet transform is performed with a Gaussian mother wavelet, resulting in a multiresolution analysis (FIG. 4E for yli, FIG. 4F for yea). Color corresponds to intensity at any given scale.
Figure 4B:
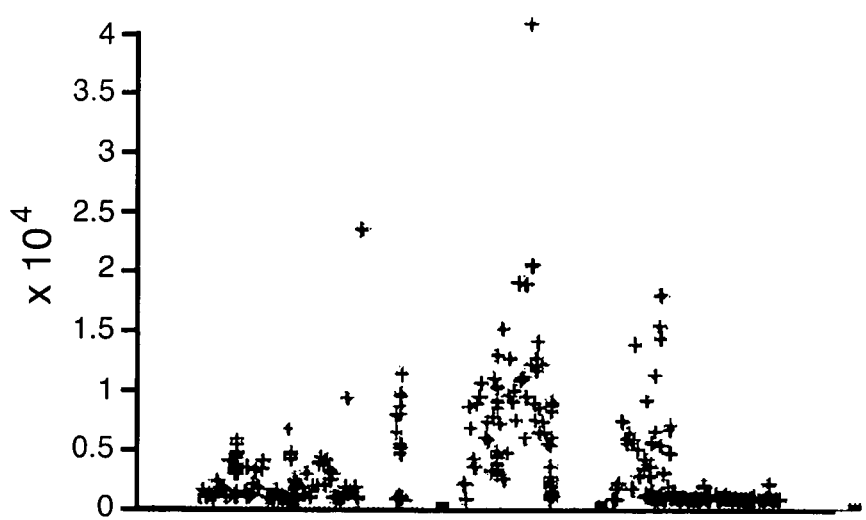
Figure 4C:
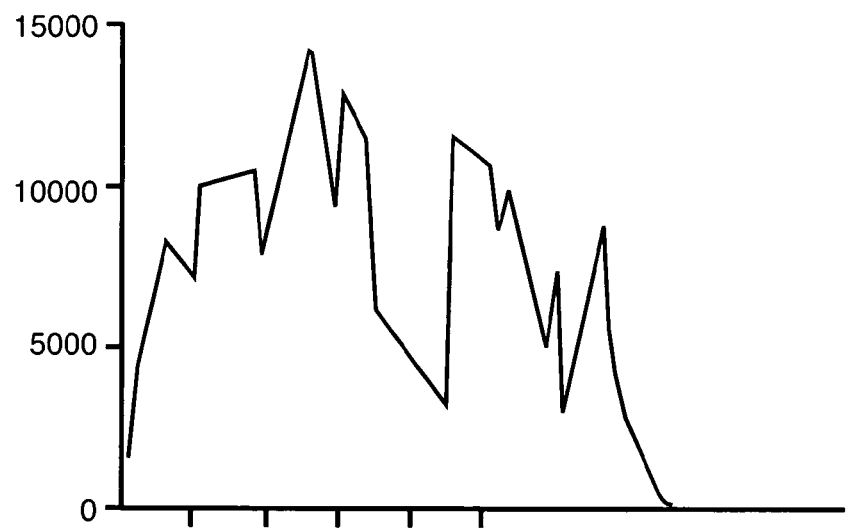
Figure 4D:
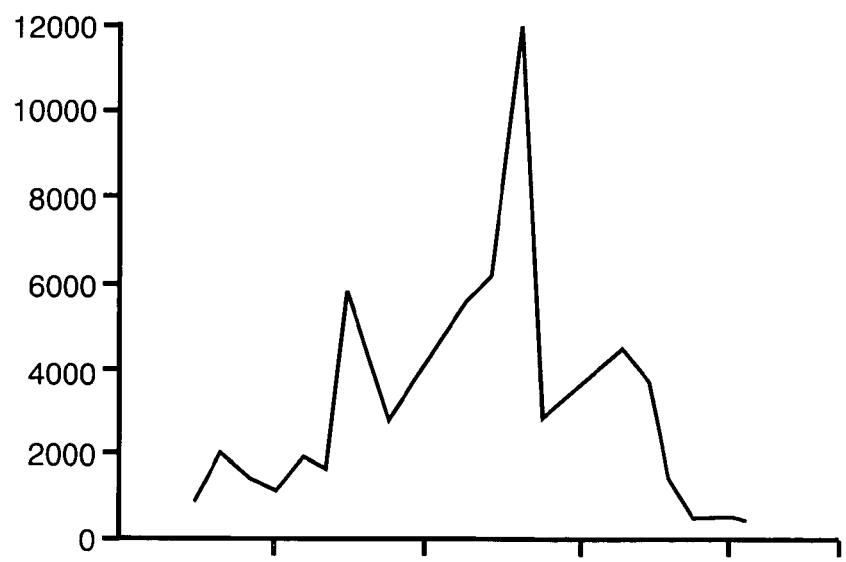
Figure 4E:
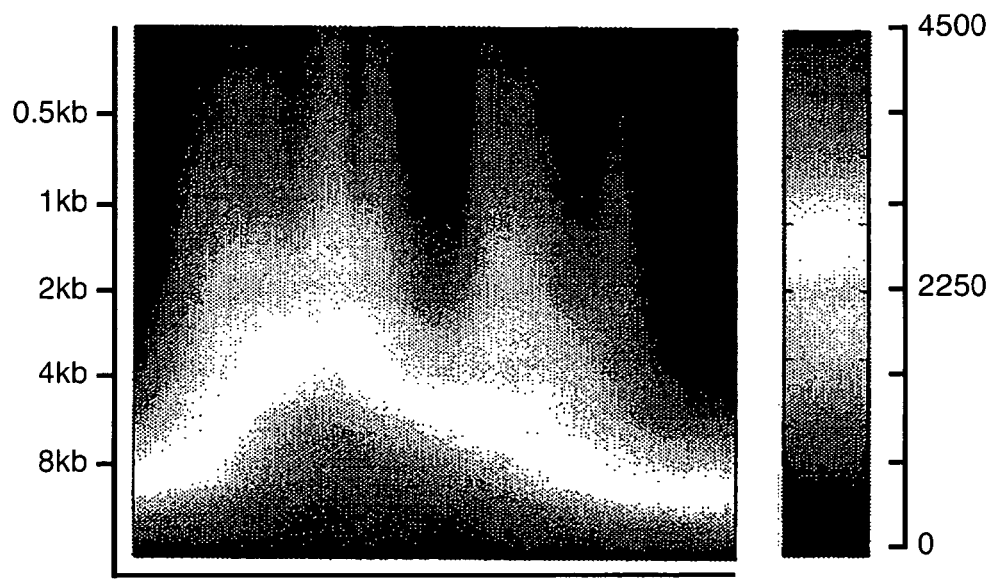
Figure 4F:
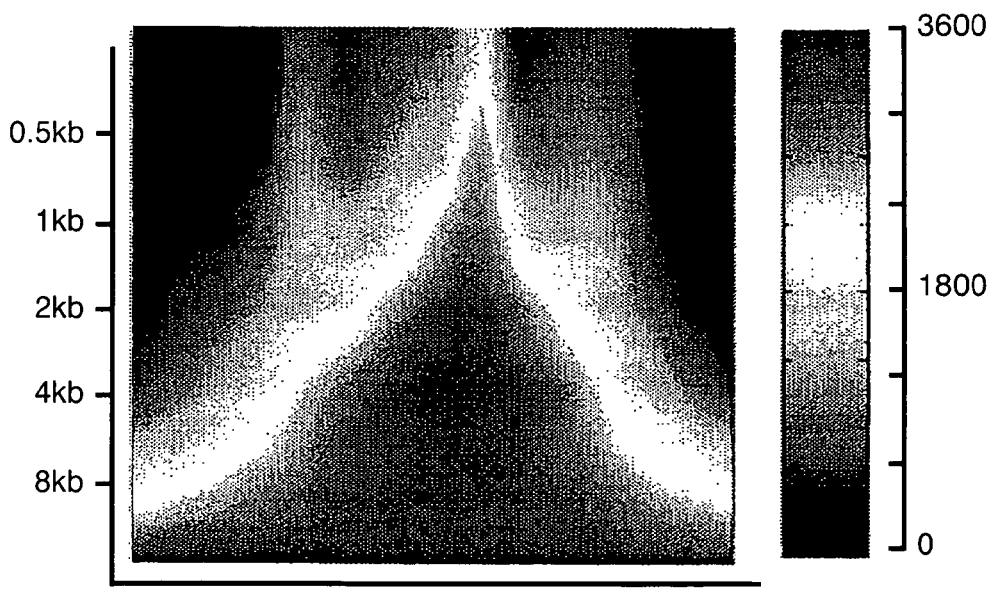
Figure 5:
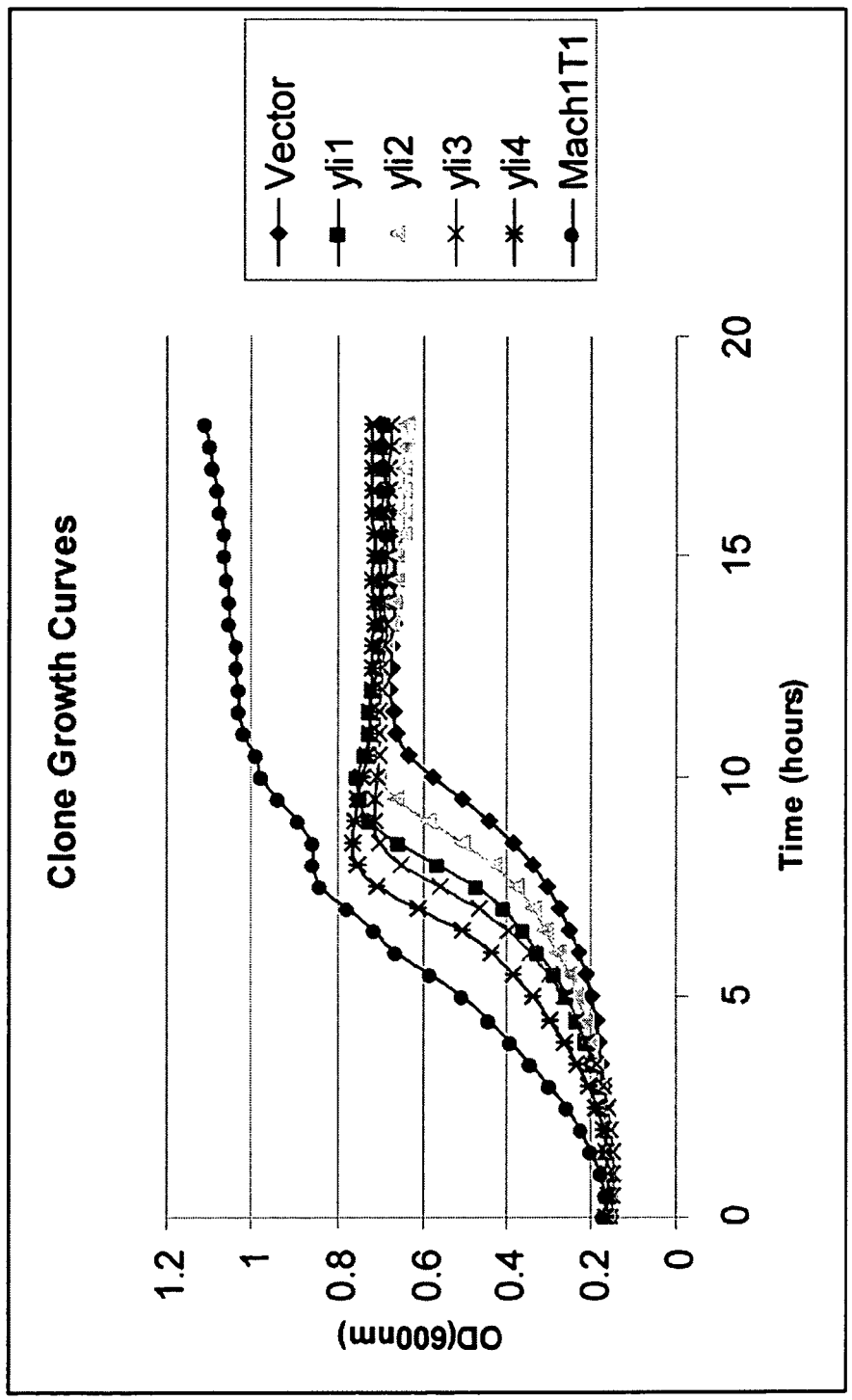
FIG. 5 illustrates growth curves of selected clones. Growth curves were measured in MOPS minimal media in 96 well format for the strain MACH1-T1 as well as the strain with vector alone and 4 clones containing pieces of the yli operon. Note: each curve is the average of greater than 20 experiments.

For each chemostat culture greater than $10^7$ clones were obtained after the transformation of these libraries into MACH1-T1 cells, once again providing adequate representation of the genome at each scale. All transformants were mixed and inoculated into chemostats containing MOPS minimal media. Cell Density was monitored in the culture as the dilution rate was systematically increased. FIG. 2 shows the increasing dilution rate and culture optical density over the time course of two cultures. Every 12 hours a sample was taken from each culture, amplified, prepared and hybridized to E. Coli Gene Chips. FIG. 3 shows an image of each chip for the 24 through 60 hour samples for each replicate. In addition a control chip of mixture of purified library DNA is shown as a starting point. A magnified panel emphasizes one of the genomic segments that is amplified, containing the yli operon. Probe level signals for each array were extracted and normalized. A wavelet based denoising scheme and multi-resolution analysis (MRA) was performed on various genome segments. FIG. 4 shows the results of the denoising and MRA for two genomic segments the yli operon and the yea operon Clones were isolated from sampling of chemostats, sequenced and growth rates calculated (FIG. 5). These results show an increase in growth predicted from the analysis.

After 60 hours of selection, the majority of the signal mapped to 5 regions of the genome (SEQ ID NO:1 through SEQ ID NO:5, listed below) corresponding to five members of paralogous gene group 117 from E. Coli K12. These genes are adrA, yliF, ydeH, yeaP, yddV. They all encode a GGEDF domain, which synthesizes cyclic-di-GMP. This bacterial second messenger is involved in cellular development and may have a role in the cell cycle. In order to confirm the growth phenotypes, growth curves were obtained with replicates using a 96 well plate reader, running KC4 v3.1 (Biotek) using the kinetic mode (incubating at 37° C., and shaking intensity-medium) with readings taken every 30 minutes. A 1% v/v of overnight culture was used to inoculate 200 µl of MOPS minimal media plus kanamycin, in a flat bottom 96 well plate. Optical density measurements were recorded at 977 nm, 900 nm, and 600 nm, and then adjusted according to the manufacturers instructions (adjusted 600=600/((977−900)/0.18)). The adjusted 600 nm reading was used for construction of growth curves. Maximal growth rates were calculated from these curves. Growth rate was calculated as the maximal slope in log scale comprising at least 4 time points (2 hours). Clones carrying these genes not only grow faster, but in addition form cellular groups and films at higher cell densities (data not shown).

Figure 6:
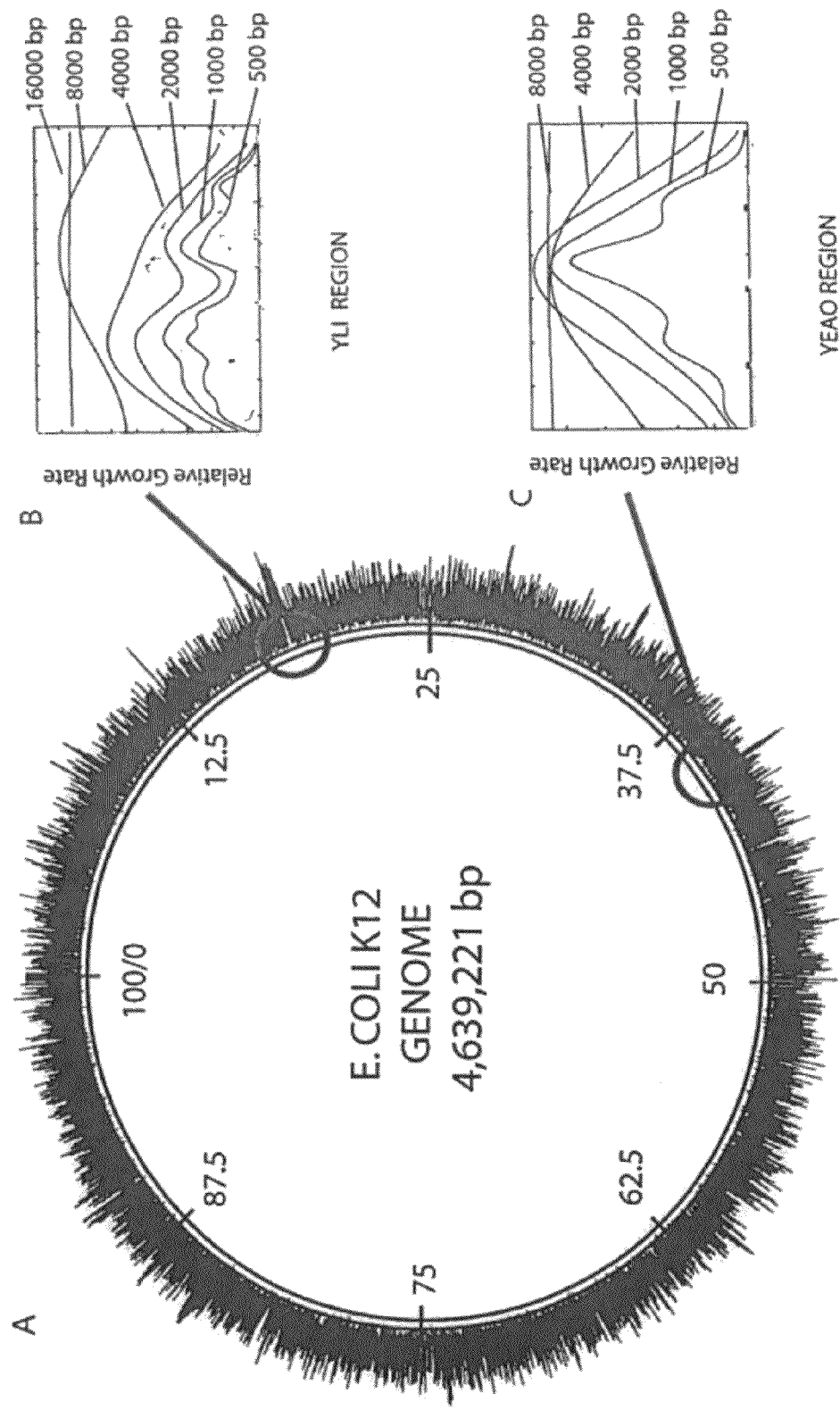
FIG. 6 shows an exemplary genome-wide scan for growth rate conferring elements, as a function of insert size.
Figure 7:
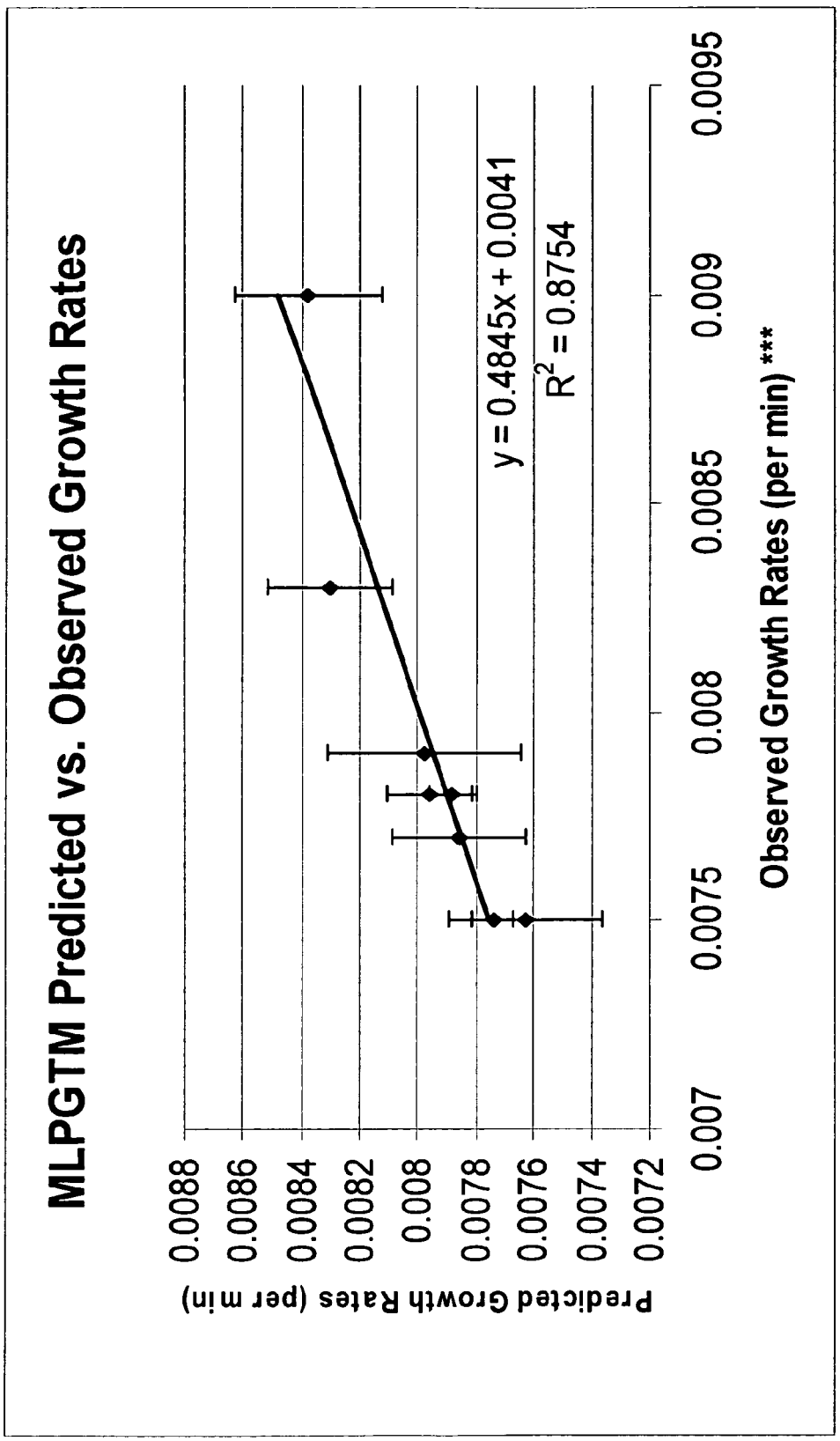
FIG. 7 shows an exemplary plot of MLPGTM predicted versus observed growth rates for genetic elements from E. coli K12.

Having measured several growth rates, it is possible to calculate the growth rates associated with all scales and positions along the genome that had nonzero signals. This was performed with the following formula. $\mu=\mu^*-\ln(R^*/R)/(\Delta time)$, where $\mu$ is the growth rate of a scale and position with a ratio of signal intensities over a time period ($\Delta time$) of R. $\mu^*$ and $R^*$ are the same known values. This calculation can be performed on a genome wide scale. FIG. 6 shows an exemplary plot of a subset of growth rates around the genome, with the yli and yeao regions amplified. A plot of MLPGTM predicted versus observed growth rates is shown in FIG. 7.

Discussion

ML-PGTM is a powerful and useful method for library selections. The method requires technical precision. Libraries of very defined sizes with minimal chimeras are necessary for clear final mathematical analysis. The libraries must also consist of enough clones to be representative of the genome. A truly representational library requires a bias free stable cloning vector. For this reason we have used vectors which contain transcriptional terminators flanking the multiple cloning site. In this way we ensure adequate representation.

Another factor in the accuracy of the method concerns the probe density of the microarrays. The current E. Coli antisense arrays available from Affymetrix were designed for transcriptional profiling experiments. As a result the arrays have a highly variable probe density along the genome. The limitation to this is that is if any plasmids representing regions with no or a low number of probes are enriched, they may be misrepresented in the signal or absent altogether.

We have demonstrated the utility of the MLPGTM method in a mapping of growth rates in minimal media across the entire genome as well as by pinpointing genomic segments that confer a selective advantage. This method can also be readily extended to other selection schemes such as antibiotic resistance and metabolite or substrate tolerance. This selection strategy could be applied to any library to be screened regardless of origin.

What is claimed is:

1. A method to identify a genetic element that confers a trait of interest, said method comprising:
subjecting a mixture of cell lines to a selection criteria that selects for the trait of interest thereby producing one or more selection-based enriched cell lines, wherein each of the cell lines in the mixture of cell lines is previously transformed with a library of one or more inserts of an approximate pre-determined insert size that is different from the insert size of the libraries used to transform the other cell lines; and
determining the relative amount of DNA of each insert size that corresponds to each of a plurality of genomic positions thereby identifying a genetic elements responsible for the trait of interest.

2. The method of claim 1, further comprising hybridizing DNA from the enriched cell lines to a microarray device.

3. The method of claim 1 wherein the trait of interest is a phenotypic trait.

4. The method of claim 1, wherein the trait of interest is an enhanced growth rate, antibiotic resistance, metabolite tolerance or substrate tolerance.

5. The method of claim 1, wherein each of the libraries has a pre-determined target insert sizes of approximately 0.5, 1.0, 2.0, 4.0 or 8.0 kilobases (kb), and the size of each insert within as given library is approximately equal to the pre-determine target insert size for such library.

6. The method of claim 1, wherein the genetic element is an open reading frame or an operon.

7. The method of claim 1, wherein the insert size between the different libraries varies by a multiple of 2.

8. The method of claim 1, wherein each cell line of the multiple of cell lines is transformed with inserts representative of an entire genome.

9. The method of claim 1, wherein an increase amount of DNA at a first genomic position indicates that the first genomic position is the genomic element that confers the trait of interest.

10. The method of claim 1, wherein the determining comprises identifying unique signal intensity patterns along the genome.

11. The method of claim 10, wherein a unique signal intensity indicates a combination of genes or regions that confers the trait of interest.

12. The method of claim 2, further comprising plotting microarray probe level signals as a function of genome position.

13. The method of claim 1, wherein the determining comprises using a computer readable medium to perform a wavelet based multi-resolution analysis.

14. The method of claim 13, wherein the wavelet based multi-resolution analysis decomposes the signal into scales of signal contribution from each of the different insert size libraries.

* * * * *

SEQUENCE LISTING

```
<160> NUMBER OF SEQ ID NOS: 7

<210> SEQ ID NO 1
<211> LENGTH: 11837
<212> TYPE: DNA
<213> ORGANISM: Escherichia coli

<400> SEQUENCE: 1
```

```
ctctgcggta gtcaggcgag ttcccgccgg gaaaacaacc gcacctgcag agatatcttc     60
accgcgacgg cgaatatttt gcccgctacg cacttcagca gtaaaacgca cgccattgtc    120
catttgttca gtctgctcct gcatcaccac cgcttcgcag ccttccggca ccggcgcacc    180
ggtcataata cgaatgcagg tacccgcagg ccattcacca tggtatggct gaccggcaaa    240
ggatttaccg gcaacgggca gcggttgccc ggaggcaata tcggctaaac gcaccgcgta    300
gccgtccatt gcggagttat caaaccccgg aacatcaagc ggcgaaacga catcgctcgc    360
cagaatacga ccaaaacact gtaccagtgg cagcgtttcc tgggcggtca gtgggtgac    420
gcgagaaagc atctcattaa gcgcggtgtc gagcgacatc aatccggtgg taaattccat    480
gaaaacactc ctgcggaggc aaaatcgaat ttgcctatta tgtcagaaaa acgccacaga    540
ctgtatgcca cctcgggcgt agcgctgggt cctgccttta catgccatat ccatctttct    600
atattcaaaa attgaatgag taattcataa aaattctgat attatatagca aaagtggcga    660
accacccttt atggacgaat actatgggca aagcagtcat tgcaattcat ggtggcgcag    720
gtgcaattag ccgcgcgcag atgagtctgc aacaggaatt acgctacatc gaggcgttgt    780
ctgccattgt tgaaaccggg cagaaaatgc tggaagcggg cgaaagtgcg ctggatgtgg    840
tgacggaagc ggtgcgtctg ctggaagagt gtccactgtt taacgccgga attggcgctg    900
tctttacgcg tgatgaaacc catgaactgg acgcctgtgt gatggatggt aacaccctga    960
aagccggtgc ggtggcgggc gttagtcatc tgcgtaatcc ggttcttgcc gcccggctgg   1020
tgatggagca aagcccgcat gtgatgatga ttggcgaagg ggcagaaaat tttgcgtttg   1080
ctcgtggcat ggagcgcgtc tcgccggaga ttttctccac gtctttgcgt tatgaacaac   1140
tactggcagc gcgcaaggaa ggggcaaccg tcctcgacca tagcggtgcg ccactggatg   1200
aaaaacagaa aatgggcacc gtgggggccg tggcgttgga tttagacggc aatttggcgg   1260
cagccacgtc cacaggcgga atgaccaata aattacccgg acgagttggc gatagtccct   1320
tagtgggtgc cggatgctac gccaataacg ccagtgtggc ggtttcttgt accggcacgg   1380
gcgaagtctt catccgcgcg ctggcggcat atgacatcgc cgcgttaatg gattacggcg   1440
gattaagtct cgcggaagcc tgcgagcggg tagtaatgga aaaactccct gcgcttggcg   1500
gtagcggtgg cttaatcgct atcgaccatg aagggaatgt cgcgctaccg tttaacaccg   1560
aaggaatgta tcgcgcctgg ggctacgcag gcgatacgcc aaccaccggt atctaccgtg   1620
aaaaagggga caccgttgcc acacagtgat gaacttgatg ccggtaatgt gctggcggtt   1680
gaaaatctga atattgcctt tatgcaggac cagcagaaaa tagctgcggt ccgcaatctc   1740
tcttttagtc tgcaacgcgg tgagacgctg gcaattgttg gcgaatccgg ctccggtaag   1800
tcagtgactg cgttggcatt gatgcgcctg ttggaacagg cgggcggttt agtacagtgc   1860
gataaaatgc tgttgcagcg gcgcagtcgc gaagtgattg aacttagcga gcagaacgct   1920
gcacaaatgc gccatgttcg cggtgcggat atggcgatga tatttcagga gccgatgaca   1980
tcgctgaacc cggtatttac tgtgggtgaa cagattgccg aatcaattcg tctgcatcag   2040
aacgccagtc gtgaagaagc gatggtcgag gcgaagcgga tgctggatca ggtacgcatt   2100
cctgaggcac aaaccattct ttcacgttat ccgcatcaac tctctggcgg gatgcgccag   2160
cgagtgatga ttgcgatggc gctgtcatgc cgcccggcgg tgctgattgc cgatgagcca   2220
accaccgcgc tggatgtcac tattcaggcg cagatcctgc aattaatcaa agtattgcaa   2280
aaagagatgt cgatgggcgt tatctttatc actcacgata tgggcgtggt ggcagagatt   2340
gccgatcggg tactggtgat gtatcagggc gaggcggtgg aaacgggtac cgtcgaacag   2400
```

```
atttttcatg caccgcaaca tccttacacc cgtgcgctgt tagctgctgt tccgcaacct    2460
ggtgcgatga aagggttaga ttatccccga cgtttcccgt tgatatcgct tgaacatcca    2520
gcgaaacagg ccccccccat cgagcagaaa acggtggtgg atggcgaacc tgttttacga    2580
gtgcgtaatc ttgtcacccg tttcccttg cgcagcggtt tgttgaatcg cgtaacgcgg     2640
gaagtgcatg ccgttgagaa agtcagtttt gatctctggc ctggcgaaac gctatcgctg    2700
gtgggcgagt ctggcagcgg taaatccact accgggcggg cgttgctgcg cctggtcgaa    2760
tcgcagggcg gcgaaattat ctttaacggt cagcgaatcg ataccttgtc acccggcaaa    2820
cttcaggcat tacgccggga tattcagttt attttttcagg acccttacgc ttcgctggac    2880
ccacgtcaga ccatcggtga ttcgattatc gaaccgctgc gtgtacacgg tttattgcca    2940
ggtaaagacg cggctgcacg cgttgcgtgg ttgctggagc gcgtgggcct gttacctgaa    3000
catgcctggc gttacccgca tgagttttcc ggcggtcagc gccagcgcat ctgcattgct    3060
cgcgcgttgg cattgaatcc aaaagtgatc attgccgacg aagccgtttc ggcgctggat    3120
gtttctattc gcgggcagat tatcaacttg ttgctcgatc tccagcgtga tttcggcatt    3180
gcgtatctgt ttatctccca cgatatggcg gtggtagagc ggattagtca tcgtgtggcg    3240
gtgatgtatc tcgggcaaat tgttgaaatt ggtccacggc gcgcggtctt cgaaaacccg    3300
cagcatcctt atacgcgtaa attactggcg gcagttccgg tcgctgaacc gtcccgacaa    3360
cgaccgcagc gtgtactgct gtcggacgat cttcccagca atattcatct gcgtggcgaa    3420
gaggtggcag ccgtctcgtt gcaatgcgtc gggccggggc attacgtcgc acaaccacaa    3480
tcagaatacg cattcatgcg tagataacat tcaggcggag aataaaatgg caagagctgt    3540
acaccgtagt gggttagtgg cgctgggcat tgcgacagcg ttgatggcat cttgtgcatt    3600
cgctgccaaa gatgtggtgg tggcggtagg atcgaatttc accacgctcg atccgtatga    3660
cgcaaatgac acgttatctc aggccgtagc gaaatcgttt taccagggc tgttcggtct     3720
ggataaagag atgaaactga aaacgtgct ggcggagagt tataccgttt ccgatgacgg      3780
cattacttac accgtgaaat tgcgggaagg cattaaattc caggatggca ccgatttcaa    3840
cgccgcggcg gtgaaagcga atctggaccg ggccagcgat ccggcgaatc atcttaaacg    3900
ctataacctg tataagaata ttgctaaaac ggaagcgatc gatccgacaa cggtaaagat    3960
taccctcaaa cagccgttct cagcgtttat taatattctt gcccatccgg cgaccgcgat    4020
gatttcaccg gcagcgctgg aaaaatatgg caaggagatt ggtttttatc cggtgggaac    4080
cggaccgtat gaactggata cctggaatca gaccgatttt gtgaaggtga aaaaattcgc    4140
gggttactgg cagccaggat tgcccaaact ggacagcata acctggcgtc cggtggcgga    4200
taacaacacc cgcgcggcaa tgctgcaaac cggtgaagcg cagtttgctt tccccattcc    4260
ttacgagcag gccacactgc tggagaaaaa caaaaatatc gagttgatgg ccagtccgtc    4320
aattatgcag cgttatatca gtatgaacgt gacgcaaaag ccgttcgata cccgaaggt     4380
ccgtgaggcg ctgaattacg ccattaaccg tccggcgctg gtgaaagttg cctttgcggg    4440
ctatgcaacg ccagctactg gtgtggtacc gccaagtatc gcctacgcgc aaagttataa    4500
accgtggcct tacgatccag tgaaagcgcg cgaattactg aaagaggcgg gatatcccaa    4560
cggtttcagt accacgctgt ggtcgtcaca taaccacagc accgcgcaga aagtgctgca    4620
atttacccag cagcagttag cgcaggtcgg gattaaagcc caggtgactg cgatggatgc    4680
cggacagcgg gcgcagaaag ttgaaggtaa agggcaaaaa gagagcggcg tgcggatgtt    4740
ctacactggc tggtcggctt caaccggcga agcggactgg gcactatcgc cgctgttttgc   4800
```

```
ctcgcagaac tggccaccga cgctgtttaa taccgcgttt tacagcaata aacaggtgga    4860
tgacttcctg gctcaggcac tgaaaactaa tgatccggcg gaaaagaccc gcttatataa    4920
ggcggcgcag gatatcatct ggcaagaatc gccgtggatc ccgctggtgg tagaaaaact    4980
ggtgtcggca cacagtaaaa acctgaccgg ttttggatc atgccagaca ccggcttcag    5040
ctttgaagac gcggatttgc aataagcaac gcagggagtg gaatgcttaa ttacgttatc    5100
aaacgcttac tggggttgat tccgacgctg tttatcgtct cggtgctggt gttttattt    5160 gtccatatgc tgcccggcga tccgcgcga ttgattgccg ggcccgaagc tgatgcgcag    5220
gttatagaac tggtgcgtca gcagctgggg ttggatcagc cgctgtatca ccagttctgg    5280
cactatatca gcaatgctgt gcaggggat tttggcctgt cgatggtgtc gcgtcgtccg    5340
gttgccgatg agattgccag ccgctttatg ccaacgctgt ggctgaccat aaccagtatg    5400
gtctgggcgg ttatatttgg tatgcggcg ggaattatcg ccgccgtctg gcgtaaccgt    5460
tggccggatc gattgagtat gaccattgcg gtgtcgggga tctcgtttcc ggcatttgct    5520
ctggggatgc ttttaattca ggtattctcc gttgaactgg gctggctgcc taccgtggga    5580
gcagacagtt ggcagcacta cattttaccc tccctgacgc tcggcgcggc agtggccgcc    5640
gtgatggcgc gctttacccg cgcgtcgttt gtcgatgttt taagcgaaga ttatatgcgt    5700
accgcgaggg cgaaaggggt gagcgaaacc tgggttgtcc tcaaacacgg gctacgtaac    5760
gcgatgatcc cggtagtgac catgatgggc ttacagtttg cttttttgct cggtggttcc    5820
atcgttgtgg agaaagtttt caactggccg ggacttggac gcttactcgt tgactccgta    5880
gaaatgcgtg attacccggt gattcaggcg gaaattctgc ttttctcgct ggaatttatt    5940
cttatcaact tagtggtgga tgtgctttac gccgccatta acccggctat caggtacaag    6000
taaggatgcg actatttaac tggcgacgtc aggcggtgtt aaacgccatg ccactggtca    6060
aacctgacca gtacgtaca ccgtggcatg aattctggcg acgatttcgc cgtcagcata    6120
tggcgatgac cgccgcatta ttcgttattt tattgattgt ggtggccatt tttgcacgct    6180
ggatcgctcc ctatgacgcc gaaaattatt ttgattatga caatctgaat aacggacctt    6240 cttttgcagca ctggtttggc gtcgattcac tggggcgtga cattttcagc cgtgtcctgg    6300
ttggtgcgca aatctcgctg gcggcggggcg tgtttgccgt gtttatcggt gcggcgatcg    6360
ggacgttgct gggcttgctc gctggatatt atgaaggctg gtgggatcgg ctgatcatgc    6420
gcatttgcga tgtgctgttt gccttcccgg gtatttttact ggcgatcgct gttgttgcgg    6480
tgttgggaag cggcattgct aacgtgatta ttgcagtcgc catttttcc atccccgcgt    6540 ttgcccgcct ggtgcgcggc aacacgctgg tgttgaaaca gcaaaccttt attgagtcag    6600
cacgcagtat tggtgccagc gatatgaccg ttttgttgcg tcatatcctg cctgggaccg    6660
tctcttctat cgtggtgttt ttcaccatgc gcattggtac ctcgattatc tctgccgcca    6720
gcctctcatt tctcggcctc ggtgcgcagc cgccgacacc agagtgggga gcaatgctca    6780
atgaggctcg agcggatatg gttatcgcgc gcatgtcgc tgttttttccg gccctggcta    6840 tttttctgac cgtactggcg ttcaatttgt tgggcgatgg tttacgcgat gcgctggatc    6900
cgaaaattaa aggatagtta cgtttgaata ttgcttgaaa gggtaatcac ctcacaggaa    6960
attattgccc taagcaagtg ttgtaacttt ctgctgattt tgtagaatcg ggtaatttgg    7020
ttaaaaagcc gcagcaaggg acaatttttg cagcggcaca gcgttcagat agttattttg    7080
ttaaatgtat taacatgctg agtttatacg aaaagataaa gataaggctg ataatttat    7140 tttttattggc agcactgtca tttattggtc ttttttttcat cattaactat caactggtat    7200
```

```
cggagcgcgc ggtaaaacgt gccgatagcc gctttgaact tattcagaaa aacgttggct   7260
atttctttaa agatattgaa cgttcggccc tgacattaaa ggactcactg tatttattaa   7320
aaaatacaga ggagattcaa cgcgccgtga ttcttaaaat ggaaatgatg ccatttttag   7380
actcggtggg actggtactt gatgataata aatattatct ttttcgcgg agggcgaatg    7440 ataaaatcgt tgtttatcat caggaacaag taaatggacc gcttgtcgac gagtcagggc   7500
gggttatttt tgccgatttt aacccatcga aacgaccgtg gtcggtggct tcagatgact   7560
ctaacaacag ctggaatccg gcatacaatt gctttgatcg tccgggtaaa aaatgtatct   7620
cttttacgct acacatcaac ggcaaagatc acgatttgtt agcggtggat aaaattcatg   7680
tcgatttaaa ctggcgatat ctgaacgagt atcttgatca aatcagcgct aatgatgaag   7740
ttctattttt gaaacaaggc catgagatca ttgccaagaa tcaactcgct cgtgaaaaac   7800
tgattattta taatagcgaa ggtaattata atattattga ttctgtcgat actgaatata   7860
tcgaaaaaac atcagcggtg ccaaacaacg cattattcga atctatttt tattatcctg    7920 gcggtaattt attgaacgca tcagataaac ttttttatct gccgtttgcg ttcattatta   7980
tcgtattgct ggtggtttat ttaatgacca ctcgtgtgtt ccgtcggcaa ttttctgaaa   8040
tgacagagct ggttaatacg ctggcgtttt tgcctgactc aacggatcaa atcgaggctc   8100
tgaaaattcg tgaaggcgat gcgaagagag ttatcagcat caaaaattcg atcgcggaaa   8160
tgaaagatgc cgaaattgaa cggtcaaata aattgctctc actgatctct tacgatcagg   8220
aaagtggttt tattaaaaat atggcgatta ttgagtctaa caataatcag tatctggctg   8280
tggggatcat caaactgtgt ggtctggaag ccgtggaagc ggtgtttggt gttgatgagc   8340
gcaataaaat cgtcaggaaa ttgtgtcagc gaattgccga gaaatatgcg caatgctgcg   8400
atatcgtgac attcaatgcc gatctctatt tacttctgtg tcgggaaaat gtacagacat   8460
ttacccgtaa aatagcgatg gtaaacgatt ttgacagcag ctttggctac cgcaatctgc   8520
gcatccataa gtctgccatt tgtgaacctt gcaggggga aaacgcctgg agttacgcag    8580
aaaaactgaa actggcgatt tccagtatcc gtgaccatat gttctcagag tttatttct    8640 gtgatgacgc gaaactcaac gaaatagaag agaatatctg gattgcgcgt aatattcgcc   8700
atgcaatgga aattggcgaa ctattcctcg tctatcaacc gatcgttgat attaacaccc   8760
gcgccattct gggcgcggag gcgttgtgcc gttgggtgtc tgcggagcgg gggatcattt   8820
caccgctgaa gttcattacc attgctgaag atatcgggtt tatcaatgag ctgggttatc   8880
agattattaa aacggcaatg ggtgaattca gacattttag tcagcgtgcg tcgctgaagg   8940
atgatttctt actgcatatt aatgtttcgc cctggcagtt aaacgaacca cactttcatg   9000
agcgttttac caccatcatg aaagaaaatg gcctgaaggc gaacagcctc tgtgttgaga   9060
tcactgaaac cgtgatcgag cgaattaatg aacattttta tctcaatatt gaacaactgc   9120
gtaaacaagg ggtacggata tcgattgatg actttggcac cggtttgtca aacctgaaac   9180
gtttttatga aattaatcca gacagcataa aggtggactc gcaattcacc ggcgatattt   9240
tcggtactgc gggaaaaatt gtgcgcatta ttttcgacct ggcacgctat aaccggatcc   9300
cggtgattgc ggaaggcgta gagagcgaag acgttgcgcg cgaattaatc aaattaggat   9360
gtgttcaggc tcagggtat ctgtaccaga aacccatgcc attctccgcc tgggataaaa    9420
gtggaaaatt agtaaaagag tagtttacgt atgtccagaa tcaataagtt cgtacttaca   9480
gtcagtctgc tgatttttat catgatttca gcagttgcct gcgggatcta cactcaaatg   9540
gtaaaggaac gggtgtatag cctgaaacag tccgttattg atactgcttt tgcggtggca   9600
```

```
aatattgctg aatatcggcg tagcgtggca attgatctta tcaacacgct aaatcccacg    9660
gaggaacagc tgttggttgg tttgcgcaca gcttacgccg actcggtttc cccctcttat    9720
ttgtacgatg tcggtcctta tctgatttcc agtgacgaat gtattcaggt aaaggagttc    9780
gagaaaaatt attgtgcaga tattatgcag gttgtgaagt atcgacatgt caaaaataca    9840
gggtttatct cttttgacgg taaaaccttc gtctattacc tctatccggt aactcacaat    9900
cgtagtctga tatttttgct tggtctggag cgttttctt tactgtcaaa atcgctggcg    9960
atggacagcg agaacctgat gttctctcta tttaagaacg gtaaaccggt gaccggtgat    10020
gaatataatg ctaaaaacgc catcttcacc gtttcggaag cgatggagca cttcgcctat    10080
ttgccgaccg gattgtatgt atttgcgtat aaaaaagatg tttatttgcg ggtttgtaca    10140
ttgattattt tctttgccgc attggtgcga gtgatatcgg gtgccagttg cctctatctg    10200
gtacgcagag tgattaatcg tggtattgtg gagaaagaag ccatcattaa taaccatttt    10260
gaacgcgtac tggatggcgg gcttttcttt tcggctgccg atgtcaaaaa actctacagt    10320
atgtataact cggcgttcct ggacgacctg accaaagcaa tgggcagaaa atcctttgac    10380
gaagatttaa aagcgctgcc ggaaaaaggc ggttatttgt gcctgtttga cgtcgataaa    10440
ttcaaaaaca ttaacgacac cttcggtcat ttgctgggcg atgaagtgtt gatgaaagtg    10500
gtgaaaatcc ttaaatcaca gatcccggta gataaaggta aagtctaccg cttcggcggt    10560
gacgaatttg cggtgattta tacgggtgga acgctggaag agttgctatc gattctaaaa    10620
gaaatcgttc atttccaggt gggaagcatt aatttaagta ccagtatcgg tgtagcacat    10680
tcaaatgaat gtcctaccgt cgaacgcttg aaaatgctgg cggatgagcg gctgtataag    10740
agtaagaaaa acggcagggc acagattagc tggcagtaat cattattcgc aggccggaca    10800
aatgattttg cccggcctga attaattaaa cccggctacc ccacaaatcg tactcatcgg    10860
cgtgctcgac tttcacacgc aggatatcac ccggcttaac gttggtttca ccattgagat    10920
aaaccgcgcc gtcgatttcc ggtgcatctg ccatgctgcg accaatcgcg ccttcttcgt    10980
ccacttcgtc gataatcacc agaatttcac ggcccacttt ctcttgcagg cgctcggcg    11040 aaatctgctg ctgcagctgc atgaaacggt tccagcgttc ttctttaact tcttccggaa    11100
cctggtcagg cagggcattg gcgtctgcac cttcaaccgg gctgtattta aagcagccaa    11160
cgcgatccag acgcgcttct ttcaggaagt cgagtagcat ctggaaatct tcttctgtct    11220
cgccagggaa gccgacaata aaggttgagc gtagggtcag ttccgggcag atttcgcgcc    11280
actgtttgat gcgcgccagt tggcgatcta cagaacccgg acgcttcatc agtttgagaa    11340
tgcgcgggct ggcgtgctgc aacggaatgt ccagatacgg caggattttg ccttctgcca    11400
tcagtgggat gacgtcgtcc acatgcggat aagggtaaac gtagtgcaga cgtgtccaga    11460
tccccagttt cgataactgt tcgcacaggc tgaccatgct ggttttacc ggctcgccgt    11520 tgtggaagcc agtacgatgt ttaacatcaa cgccataggc ggaagtatcc tgcgagatca    11580
ccagaatctc tttaacgccc gcatctacca gacgttcgc ttcacttaac acttcgccaa    11640
tcggacggct caccaggtcg ccgcgcatag acggaataat gcagaaggtg cagcggtgat    11700
tacagccttc agaaattttc agataggcat aatgacgcgg cgtcagtttc acaccttgtt    11760
ctggcaccag gctcaggaat gggttgtgtt tcggttttgg cacgtagtga tgaacgtgct    11820
ccagaacctg ctcatag                                                  11837
```

<210> SEQ ID NO 2
<211> LENGTH: 3073

<212> TYPE: DNA
<213> ORGANISM: Escherichia coli

<400> SEQUENCE: 2

| | | | | | |
|---|---|---|---|---|---|
| ctccgtctct | ataatttggg | aaaattgttt | ctgaatgttc | ccaaaaataa tgaatgatga | 60 |
| aaacttttc | aaaaaagcgg | cggcgcacgg | ggaggaacct | cctttaactc ctcaaaacga | 120 |
| acatcagcgg | tccgggctgc | gcttcgcccg | tcgcgtcaga | ctaccccgtg cggttggcct | 180 |
| ggctggcatg | ttcttaccga | ttgcttcaac | gctggtttca | cacccgccgc cgggctggtg | 240 |
| gtggctggtg | ttggtcggct | gggcgttcgt | ctggccgcat | ttagcctggc agatagcgag | 300 |
| cagggccgtc | gatccgctta | gccgggaaat | ttacaactta | aaaaccgatg cagtattagc | 360 |
| gggaatgtgg | gtaggcgtaa | tgggcgtaaa | cgtgctgcct | tccaccgcga tgttgatgat | 420 |
| tatgtgtctg | aatttgatgg | gggcaggcgg | ccccgtctg | tttgtcgcgg gtctggtgtt | 480 |
| gatggtggtt | tcctgccttg | tcaccctcga | gctgacgggc | attaccgtgt cgttcaatag | 540 |
| tgcgccgctg | aatggtggc | tctcccttcc | cattattgtc | atttatcctc tgctgtttgg | 600 |
| ctgggtcagc | taccagacgg | caaccaaact | ggcggaacat | aaacgcaggt tgcaggtcat | 660 |
| gagtacccgc | gacggcatga | cgggcgtgta | taaccgacgt | cattgggaaa ctatgttacg | 720 |
| caatgaattt | gataactgtc | ggcggcataa | tcgcgatgca | acgttactga ttatcgatat | 780 |
| cgaccatttc | aagagcatca | acgatacctg | gggccatgat | gtgggcgatg aagcgattgt | 840 |
| ggcgcttacc | cgacagttac | aaattacccct | gcgcggtagc | gatgtgattg gtcggtttgg | 900 |
| cggcgatgag | tttgcagtaa | tcatgtccgg | tacgccagct | gagagcgcca ttaccgccat | 960 |
| gttacgggtg | catgaagggc | taaatacatt | acgtttgccg | aatacgccac aggtaacttt | 1020 |
| acggattagt | gtggggttg | cgccgctgaa | cccacaaatg | agtcactatc gtgagtggtt | 1080 |
| gaaatcggca | gatttggcgc | tttacaaagc | aaagaaagcc | ggacgtaacc gcaccgaagt | 1140 |
| ggcggcctga | cgtccggcga | aagtcatcag | gatttgctga | gtttttctga ttttccata | 1200 |
| cacttcgtca | tcgcttcgat | cactgcagca | cggaagcctt | tctcttccag tacgcgtacc | 1260 |
| gcttcaatgg | tggtgcctcc | cggtgagcag | accatatctt | tcagtgcccc cggatgttct | 1320 |
| cccgttttcca | gcaccatttt | tgcggaaccc | attaccgcct | gagcggcaaa tttatacgcc | 1380 |
| tgggcgcgtg | gcatcccgcc | cagcacggcg | gcgtcggcca | tcgcttcgat aaacataaat | 1440 |
| acgtaggctg | gcgaagaacc | gctcacaccg | accaccgggt | ggatcatcgg ctcagcaatt | 1500 |
| acttccgctt | cgccaaagca | gcggaaaata | ttcagcacat | cagcggtatc ttctgggtt | 1560 |
| accagcgcgt | ttggcgttac | ggaggtcatc | ccggcattaa | ccagtgcggg agtgttcggc | 1620 |
| atggcgcgga | taattttccg | gtcatggccc | agcgcgcggg | caagctggtc gagcgtgaca | 1680 |
| cctgcagcaa | tagaaacgac | cagagagtct | ttattcaggc | tggaggtgat ttcgctaagc | 1740 |
| actttaatca | tgatgccagg | tttaacggca | gcaaaaatga | tgtcggcgat ttgcgccact | 1800 |
| tcttgcgccg | attctgcggc | gttgatgccg | aactggtcat | gcagggcggc gactttatcc | 1860 |
| ggggaggggg | tgtataccca | gatttgcccct | ggaagcacct | gaccgctggc aatcagaccg | 1920 |
| ccgagaatgg | cttttcccat | attgccgcag | ccaataaaac | cgattttctt ttccattgcc | 1980 |
| tcactcctgc | cgtgaaattc | attgttttga | taatcgctgg | cagaagcata aacagaacta | 2040 |
| tgccggaagg | caaaagcgcg | acacaataga | ggattaccca | acaaaggatg actttatgac | 2100 |
| aatttgggtg | gatgccgacg | cgtgtcccaa | tgtaattaaa | gagattttgt atcgcgcggc | 2160 |
| ggaacgtatg | cagatgccgc | tggtactggt | agcaaaccag | agtttacgcg tgccgccatc | 2220 |
| gcgatttatt | cgtacgctgc | gcgtcgcggc | aggtttcgac | gttgccgata acgaaattgt | 2280 |

```
ccggcagtgt gaagcgggcg atttggtgat caccgcagat ataccttttgg ctgctgaagc    2340 catcgagaaa ggcgctgcgg cgcttaatcc gcgcggcgaa cgttacacgc cagcgaccat    2400
tcgtgagcgc ctgacgatgc gcgattttat ggataccttta cgtgccagtg ggatccagac   2460
cggcggacca gatagccttt cacaacgtga ccgccaggcc tttgccgcgg agctggagaa    2520
gtggtggctg gaagtgcaac gtagtcgtgg ctaaatgtaa tttattattt acacttcatt    2580
cttgaatatt tattggtata gtaaggggtg tattgagatt ttcactttaa gtggaatttt    2640
ttctttacaa tcgaaattgt actagtttga tggtatgatc gctattctca tgacaccggc    2700
tttcgccgca ttgcgaccta ttggggaaaa cccacgatga cacaacctct ttttctgatc    2760
gggcctcggg gctgtggtaa acaacggtg gaatggccc ttgccgattc gcttaaccgt      2820
cggtttgtcg ataccgatca gtggttgcaa tcacagctca atatgacggt cgcggagatc    2880
gtcgaaaggg aagagtgggc gggatttcgc gccagagaaa cggcggcgct ggaagcggta    2940
actgcgccat ccaccgttat cgctacaggc ggcggcatta ttctgacgga atttaatcgt    3000
cacttcatgc aaaataacgg gatcgtggtt tatttgtgtg cgccagtatc agtcctggtt    3060
aaccgactgc aag                                                       3073

<210> SEQ ID NO 3
<211> LENGTH: 2959
<212> TYPE: DNA
<213> ORGANISM: Escherichia coli
<400> SEQUENCE: 3
ctgcagcggc actgggatcg gctatggtcg tgccgctggc tttgaacggt tttggctggc      60
aaggcgcgtt gctcatgctg atgtgttttc ctctgctggc tctttttttta tggctgccac    120 agtggcgaag tcaacaacat gcaaatttga gtacctcgcg cgccttacat actcggggta    180
tctggcgttc accgcttgcc tggcaggtca cattgttttct tgggatcaac tcactggtct   240
attacgtgat tattggctgg cttccggcga tcctcatcag tcacggctat agcgaagcac    300
aggcgggttc actgcatggt ttgctgcaac tagccacagc agcacccggt ttgctgatcc    360
cacttttctt acatcatgtg aaagatcagc gtggtattgc agcgttcgtt gccttgatgt    420
gcgcagtggg cgcggttggg ctctgctttta tgccagcgca cgcgatcacc tggactctgc   480
ttttcggttt tggttccggc gcaacaatga tactggggtt gacgttcatt ggtctgcggg    540
ctagttctgc gcatcaggcg gcggcactct cggggatggc acaatccgtc gggtatttgt    600
tggcagcctg tgggccgccg ctgatgggta aaatacacga tgctaacggt aactggtctg    660
taccacttat gggtgttgcc atactttcac tactgatggc gattttcgga ctttgcgccg    720
ggagagacaa agaaattcgc taatatccgg tgctatagtg acgtaacaaa tcatgcgtga    780
aagggagaac aaacacgatg aatattcagt gcaaacgcgt ttatgatccg gctgaacaga    840
gcgatggtta tcgcatactg gtcgaccgcc tctggccgcg cggtatcaaa aaaccgatt    900 tagcccttga tgagtgggat aaagaaatca cgccgtcaac ggaactgcgc aaagcctttc    960
acggcgaagt cgtcgattat gcaaccttttc gcagcaata tcttgcagaa ctggcgcaac   1020
acgagcaaga aggaaagcgg ctggcggaca tcgccaaaaa acagccgctg accctgctct   1080
actcagcaaa aaacaccacg cagaaccatg cgctggtgct ggccgactgg ctacgtagct   1140 tgtgattttta gtacagcatc cggcggttat ttttcaccag ccggatggtc acgccgccac   1200
```

```
aatgcccatt catcaatcgt ttcaccgccc ggtaatttgc aattgttgct gaccccttgc    1260
gctgtctgca ctggaatgag cgtcccgccc ttctgctggc aatagaccga cgccggattt    1320
gccataccaa tctgcggcgg tttaggtgct tctggctgag aaggggttga acaaccagcc    1380
aggaccagca agcaaggcag aacaaaactg ataattttca tttattgatc tcacatattt    1440
atccaagatt agagtatcgc ggtatcgttt tgttttgcag cactattttt attacattca    1500
ctcaaaacat attacgtctt gtttcatctt tgttgatgat gttttatcat gcctgcaaag    1560
attaaataat cagcatttac ccgccgtatc ctggagttgt tccgtgtcag atcagattat    1620
cgcccgcgtc tcgcaatccc ttgccaaaga acagtcactg gaaagtctgg tccgacagct    1680
tctggagatg ctggaaatgg tcactgatat ggaatcaacc tacctgacca agtggatgt    1740 cgaagcgcgc ctgcagcata ttatgtttgc ccgtaacagc cagaaaatgt catcccgga    1800 gaattttacc gtctcgtggg attactcgtt atgcaaacgc gccattgatg aaaactgctt    1860
tttcagcgat gaagtccccg accgttgggg tgactgtatt gcggcacgca atcttggcat    1920
caccacattt ctgagcacgc caattcactt accggatgga tcattctatg gcacgctttg    1980
cgccgccagc agtgagaagc gccagtggag tgaacgcgcg gaacaggttt tacagttatt    2040
cgccggactg attgcacaat atattcaaaa agaggcactg gttgaacagc tgcgcgaagc    2100
caatgctgcg ctgattgcgc aatcgtatac cgactcgtta accgggctac cgaatcggcg    2160
ggcgattttt gaaaatctga cgacactgtt ttccctcgcc cggcatctta accataagat    2220
aatgatcgcg tttatcgatc tggataactt caaattaatc aatgatcgtt ttggtcataa    2280
tagtggcgat ctgtttctca ttcaggttgg cgagcgcctt aatacgctcc agcaaaatgg    2340
cgaagttatt ggtcgtctcg gcggtgatga gttttagtt gtttcactaa caacgagaa    2400 tgcggatatt tcgtcgctgc gagaacgcat tcagcagcaa atacgtggag aatatcactt    2460
aggtgatgtt gatttgtatt atcccggtgc cagtcttggc atagtagaag tcgatcctga    2520
aacaaccgat gcagacagtg ccctgcatgc tgccgatatt gcgatgtatc aggagaaaaa    2580
acacaaacag aaaacacctt ttgtcgcgca tccagcgcta cattcctgag gcgtattcac    2640
atccttttga ttggtgataa catgcgaatc ggtattattt ttccggttgt aatcttcatt    2700
acagcggtcg tatttttagc atggtttttt attggcggct atgctgcccc gggagcataa    2760
agatgaaaaa aacaacgatt attatgatgg gtgtggcgat tattgtcgta ctcggcactg    2820
agctgggatg gtggtaacgt cacctctaaa aaatagcaaa ggctgcctgt gtgcagcctt    2880
tgtgcaattt aagcgttaac ttttaatctt cctgtagata aatagcacga caatcgcacc    2940
aataacggca accacgaag                                                 2959

<210> SEQ ID NO 4
<211> LENGTH: 2643
<212> TYPE: DNA
<213> ORGANISM: Escherichia coli

<400> SEQUENCE: 4
ctggcgaatc tgccgttctt cggtgatatc cgagaaagtc attaccaggt tctgcagatg     60
cgcgagcacg tcataaaccg ggctgataga ggctttaatc cagattttt caccggtgcg    120 cgtcaacagc agaaattcgt cctgatcgcg ggcggttttc catagcaact gttgtaaacg    180
aatgcggtta tcggcaggga attcaggaat gttcaggagt gtatcgggct gcataccgct    240
ggcttcgcta atgcagtaac caaacatttc ggtaaatgcg cgattgcact gcacaatatg    300
gcgttccgga tcgaggacaa tcaccggtcg gtcgagatgg tcaacggcaa taatcaattg    360
```

```
tcgggtctgt tcttttttgcg ccatttctac gctggcatcc cgtaccagcg ccaggtaata    420
aactttcccc tcggcgctca ctttcgatag cgcaaaacgg gtccagattt tactgccgtc    480
ttttttctcc agctgcagct cccgactcat ccccctcaaca cgcgctttac cgccttcacg    540
gttgtgacga atgtattcag gatgcgcagg acgcaaatcc cgcggaatca gcatatcaat    600
gttattgcca atgacttctt cacgtttgta tccccagagc ttctctgcgg cggggttgaa    660
aaacatcact tcatcatttt cgttaattaa caccgcaccc atcatatttt gctcaagggc    720
ggggaaaaaa atgccatcgg cggcattatc cgcatcggtt agcttcatga ttacctctgc    780
atcctggcgc atcaaagac tggctttcca gagttcaaca cggtttctac ctcgtctttt    840
ggcgatatac agagcttcat cggctatttg aatgaggcgc tcatagtcag gatgaccatt    900
aaacatggcg gcaccgatgg aaagtgagag ggcaatatct tcgccgtttg cggctttcag    960
tttggttttc tccacccgac tgcgaatacg ttctgcggta cgtaacgttt cgttttcaga   1020
agcttcagtc aaaacaatga taaattcatc gcccccgtag cggaaaacat aatcactact   1080
gcggacgttg tcataaaagg cctgagagac tttacgcaga atttcatcac cagtgttatg   1140
gccccacgta tcgttgatct ctttgaattt atcaacgtca ataatcagca ctgacagcgg   1200
tgtaccggtc cggttggcat gggcaatttc gcgtttgaag atagtcggta ggaaacggcg   1260
gttaagtaat ttcgtcagta catccatacc gacttcgtgg cgcgatactt cttcaaacaa   1320
ttcacgcagc aaggtaataa tttgcgatac ggtatttctt atctgtaata aaaatttcac   1380
ccgcagactt ctgttattca aatttctggt gttacgcatg gtttgattga aaataccgtc   1440
gaaatcctga atcagacggg agatatggcc tacttcggca ataccactaa aataatgtcg   1500
acctttatgg ttaaaccaca ggccaaaatc agcctggctt aaaggcaaac tactgcctaa   1560
atcagaatcc agcaggattt tatagataat atctatttcc catgaaagta ttgaggctat   1620
ttgccgttct ttttcttctt cggcgttttc cagtaacgag aagatacgat agttttcatc   1680
ttcctttgag gcactactgt cactaaaggt aaacgcgcga gtcatcactt ccatcgcgat   1740
atcaatactg ttaatcgaga aatggtagac ctgaagtttt tctgcggcgg aataatccga   1800
agagaagatc accggataga ggattttttt cagcaccccga aaccccatct cgacaatttc   1860
taccggaatt cctatgcggg catgcacttc cgcgacggta tgctggattt gtattagcct   1920
ttcgacatcg tcaacctggg cagaaagcac gttaataatc cagcgttcca tcgcactctt   1980
caactgccgc tcaacttgtt cattactcaa gaattcttcg gcatgcgggt cgatgcggac   2040
aattcgataa aactcgatac tcagataatg agcatgcgca acggcaattt ccgcggcttt   2100
agcacgaatg ggcggatctg cctgttcgac aagtccggtc cactcatctt tcattctttt   2160
aaaatacatc tccataattc acacccttat aaggctggga atcagacgg aatcaaaatg   2220
aaacgcaacg tgcgagatcg actaactgca ccatattctc ctgaaatatg aagatatact   2280
gaaaagaaat aagcgattta ggacagtttc aatctacgct actgttcttc agaagagtat   2340
agcccatcgt aattattttt cggtgacagc gaatatcgta tggttttttca tattcataca   2400
ttttttattag ggatttatgg ctgtttaact aagtgtggtt aatttgactt aagtaagcat   2460
gattattagt gggatagttt aagagggtaa caagccggtg ggtaaagcac cggcttgtta   2520
caaagtaaga atgggagttt aactgcccca gcgactttgc agatagctga ccgcttgttg   2580
agtctgcggt ttattcagat agtcctcacg gaacaagatg gtgccgctaa tttcgggcac   2640
agc                                                                 2643
```

<210> SEQ ID NO 5

<211> LENGTH: 1760
<212> TYPE: DNA
<213> ORGANISM: Escherichia coli

<400> SEQUENCE: 5

| | | | | | |
|---|---|---|---|---|---|
| ttgcatggat | agatttgtgt | tttgctttta | cgctaacagg | catttcctg | cactgataac | 60 |
| gaatcgttga | cacagtagca | tcagttttct | caatgaatgt | taaacggagc | ttaaactcgg | 120 |
| ttaatcacat | tttgttcgtc | aataaacatg | cagcgatttc | ttccggtttg | cttaccctca | 180 |
| tacattgccc | ggtccgctct | ccaatgacc | acatccagag | gctcttcagg | aaatgcgcga | 240 |
| ctcacacctg | ctgtcacggt | aatgttgata | tgcccttcag | aatgtgtgat | ggcatggtta | 300 |
| tcgactaact | ggcaaattct | gacacctgca | cgacatgctt | cttcatcatt | agccgctttg | 360 |
| acaataatga | taaattcttc | gcccccgtag | cgataaaccg | tttcgtaatc | acgcgtccaa | 420 |
| ctggctaagt | aagttgccag | ggtgcgtaat | actacatcgc | cgattaaatg | cccgtaggta | 480 |
| tcattaacca | atttaaatcg | gtcaatatcc | aacaacatta | aataaagatt | cagaggctca | 540 |
| gcgttgcgta | actgatgatc | aaaggattca | tcaagaaccc | gacgacccgg | caatcccgtc | 600 |
| aaaacatcca | tattgctacg | gatcgtcagc | aaataaattt | tgtaatcggt | taatgccgca | 660 |
| gtaaaagaaa | gcaacccctc | ctgaaaggcg | tcgaaatgcg | cgtcctgcca | gtgatttca | 720 |
| acaatagcca | gcattaattc | ccgaccacag | ttatgcatat | gttgatgggc | agaatccatt | 780 |
| agccgaacgt | aaggtaattc | atcgttatcg | agtggcccca | gatgatcaat | ccaccgacca | 840 |
| aactggcaca | gtccataaga | atggttatcc | gttatttctg | gcttactggc | atctctcgcg | 900 |
| accacgctgt | gaaacatact | caccagccac | tggtagtggg | catcgatagc | cttattgaga | 960 |
| tttaacaaga | tggcatcaat | ttccgttgtc | ttcttgatca | ttgccactcc | tttttcacag | 1020 |
| ttccttgtgc | gcgctattct | aacgagagaa | aagcaaaatt | acgtcaatat | tttcatagaa | 1080 |
| atccgaagtt | atgagtcatc | tctgagataa | cattgtgatt | taaaacaaaa | tcagcggata | 1140 |
| aaaaagtgtt | taattctgta | aattacctct | gcattatcgt | aaataaaagg | atgacaaata | 1200 |
| gcataaccca | ataccctaat | ggcccagtag | ttcaggccat | caggctaatt | tatttttatt | 1260 |
| tctgcaaatg | agtgacccga | acgacggccg | gcgcgctttt | cttatccaga | ctgccactaa | 1320 |
| tgttgatcat | ctggtccggc | tgaacttctc | gtccatcaaa | gacggccgca | ggaataacga | 1380 |
| cattaatttc | accgctctta | tcgcgaaaaa | cgtaacggtc | ctctcctttg | tgagaaatca | 1440 |
| aattaccgcg | tagtgaaacc | gaagcgccat | cgtgcatggt | ttttgcgaaa | tcaacggtca | 1500 |
| tttttttgc | atcatcggtt | ccgcgatagc | catcttctat | tgcatgaggc | ggcggtggcg | 1560 |
| ctgcatcctg | ttttaaaccg | ccctggtcat | ctgccaacgc | ataaggcatg | acaagaaaac | 1620 |
| ttgctaatac | aatggcctga | aatttcatac | taactcctta | attgcgtttg | gtttgactta | 1680 |
| ttaagtctgg | ttgctattt | tataattgcc | aaataagaat | attgccaatt | gttataaggc | 1740 |
| atttaaaatc | agccaactag | | | | | 1760 |

<210> SEQ ID NO 6
<211> LENGTH: 21
<212> TYPE: DNA
<213> ORGANISM: Escherichia coli

<400> SEQUENCE: 6
cagtccagtt acgctggagt c                                               21

<210> SEQ ID NO 7
<211> LENGTH: 24
<212> TYPE: DNA

```
<213> ORGANISM: Escherichia coli

<400> SEQUENCE: 7
ggtcaggtat gatttaaatg gtca                                              24
```